(12) United States Patent
Press et al.

(10) Patent No.: US 8,153,669 B2
(45) Date of Patent: Apr. 10, 2012

(54) QUATERNARY AMMONIUM SALTS AS M3 ANTAGONISTS

(75) Inventors: Neil John Press, West Sussex (GB); Stephen Paul Collingwood, West Sussex (GB)

(73) Assignee: Novartis AG, Basel (CH)

( * ) Notice: Subject to any disclaimer, the term of this patent is extended or adjusted under 35 U.S.C. 154(b) by 1295 days.

(21) Appl. No.: 11/721,989

(22) PCT Filed: Dec. 22, 2005

(86) PCT No.: PCT/EP2005/013897
§ 371 (c)(1), (2), (4) Date: Jul. 18, 2007

(87) PCT Pub. No.: WO2006/066929
PCT Pub. Date: Jun. 29, 2006

(65) Prior Publication Data
US 2009/0227590 A1 Sep. 10, 2009

(30) Foreign Application Priority Data
Dec. 24, 2004 (GB) .................................. 0428418.8

(51) Int. Cl.
A61K 31/42 (2006.01)
C07D 403/12 (2006.01)
(52) U.S. Cl. ........ 514/378; 514/317; 514/326; 514/408; 514/422; 546/212; 546/231; 548/240; 548/471; 548/527
(58) Field of Classification Search .................. 514/317, 514/326, 378, 408, 422; 546/212, 231; 548/240, 548/471, 527
See application file for complete search history.

(56) References Cited

U.S. PATENT DOCUMENTS

| | | | |
|---|---|---|---|
| 2,746,966 A | 5/1956 | Biel | 546/187 |
| 2,956,062 A * | 10/1960 | Lunsford | 548/556 |
| 4,447,439 A * | 5/1984 | Nishimura et al. | 514/217.04 |
| 7,192,978 B2 * | 3/2007 | Quinones et al. | 514/422 |
| 7,465,751 B2 * | 12/2008 | Mehta et al. | 514/422 |
| 7,504,432 B2 * | 3/2009 | Ogino et al. | 514/429 |
| 2006/0287362 A1 * | 12/2006 | Collingwood et al. | 514/317 |

FOREIGN PATENT DOCUMENTS

| | | |
|---|---|---|
| EP | 0 073 645 | 3/1983 |
| EP | 1 302 458 | 4/2003 |
| JP | 52-83763 | 7/1977 |
| JP | 54 027570 | 3/1979 |
| JP | 5-504578 | 7/1993 |
| JP | 2001-504459 | 4/2001 |
| WO | WO 92/06958 | 4/1992 |
| WO | WO 98/21183 | 5/1998 |
| WO | 03/087094 | 10/2003 |
| WO | 2005/000815 | 1/2005 |

OTHER PUBLICATIONS

Lunsford "esters . . . " CA55:38095 (1961).*

Ogino et al. "preparation of 2- . . . " Ca 136:118468 (2002).*
Collingwood et al. "Preparation of pyrrolidinium . . . " CA 142:113906 (2005).*
Patent Abstracts of Japan, vol. 005, No. 148 (C-072), (1981), & JP 56 079688 A (Ota Seiyaku KK), (1981), abstract; compounds 5-9.
Patent Abstracts of Japan, vol. 008, No. 052 (C-213), (1984), & JP 58 208270 A (Dainippon Seiyaku KK), (1983), abstract Formula (I').
Waelbroeck M et al., "Binding Propertied of Nine 4-Diphenyl-Acetoxy-N-Methyl-Piperidine (4-Damp) Analogues to M1, M2, M3, and Putative M4 Muscarinic Receptor Subtypes", British Journal of Pharmacology, vol. 105, No. 1, pp. 97-102, (1992).
Sugai S et al., "Studies on Spasmolytics. II. Synthesis and Anticholinergic Activities of 4-Acyloxy-1-Alkyl-1-(1,3-Dioxolan-4-Ylmethyl)Piperidinium Compounds", Chemical and Pharmaceutical Bulletin, Pharmaceutical Society of Japan, vol. 32, No. 3, pp. 977-985, (1984).
Sugai et al., Studies on Spasmolytics III.[1]) Synthesis and Anticholingergie Activity of 4-Acyloxy-1-(1,3-dioxolon-2-yimethyl) pyperidines and Their Quatemary Salts[2]). Chem. Pharm. Bull., vol. 32, pp. 1126-1134, 1984.
Sugai et al., Studies on Spasmolytics. VII.[1]) Pharmacological Properties of 4-Benziloyloxy-and 4-(Xanthene-9-carbonyloxy)-1-(1,3-dioxolan-2-yimethyl)-1-methylpiperidinium Salts[2]). Zasshi, vol. 105, pp. 990-995, 1985.
Yoshida et al., Structure-Activity Relationship of 3- and 4-Acyloxy-1-(1,3-dioxolan-4-yimethyl)piperdine Derivatives[1]), Chem. Phamr. Bull. vol. 33, pp. 816-822, 1985.
Waelbroeck M. et al., "Binding properties of nine 4-diphenyl-acetoxy-N-methyl-piperidine (4-DAMP) analogues to $M_1$, $M_2$, $M_3$ and putative $M_4$ muscarinic receptor subtypes", British Journal of Pharmacology, vol. 105, No. 1, pp. 97-102, 1992.
McMillian Freeman H et al., "Antispasmodics IV. Further Basic Alkyl Ester Acid Addition and Quatemary Ammonium Salts of Alpha-(2-Cycloalkenyl)-2-thienylacetic Acid", JAPA, pp. 576-581, 1956.

* cited by examiner

*Primary Examiner* — Celia Chang
(74) *Attorney, Agent, or Firm* — Cozette M McAvoy

(57) ABSTRACT

Compounds of formula (I), in salt or zwitterionic form, wherein J, L, M, $R^1$, $R^2$, $R^3$, $R^4$ and $R^5$ have the meanings as indicated in the specification, are useful for treating conditions that are mediated by the muscarinic M3 receptor. Pharmaceutical compositions that contain the compounds and a process for preparing the compounds are also described.

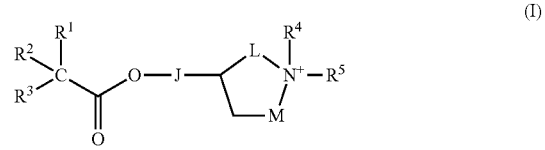

(I)

8 Claims, No Drawings

QUATERNARY AMMONIUM SALTS AS M3 ANTAGONISTS

This invention relates to organic compounds, their preparation and use as pharmaceuticals.

In one aspect the invention provides compounds of formula I

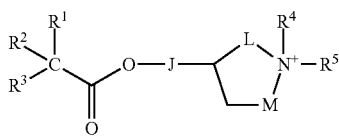

in salt or zwitterionic form wherein
L and M are (a bond and —$CH_2$—$CH_2$—), (—$CH_2$— and —$CH_2$—$CH_2$—) or (—$CH_2$—$CH_2$— and —$CH_2$—) respectively and J is $C_1$-$C_2$-alkylene,
or L and M are (—$CH_2$— and —$CH_2$—$CH_2$—) or (—$CH_2$—$CH_2$— and —$CH_2$—) respectively and J is a bond;
$R^1$ is a $C_3$-$C_{15}$-carbocyclic group or a 5- to 12-membered heterocyclic group having at least one ring heteroatom selected from nitrogen, oxygen and sulphur;
$R^2$ is hydrogen, hydroxy, or $C_1$-$C_4$-alkyl optionally substituted by hydroxy;
$R^3$ is a $C_3$-$C_{15}$-carbocyclic group or a 5- to 12-membered heterocyclic group having at least one ring heteroatom selected from nitrogen, oxygen and sulphur,
wherein $R^1$ and $R^3$ are not the same;
or —$CR^1R^2R^3$ together form a group of formula

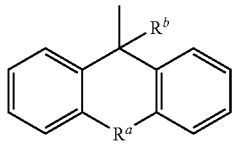

where $R^a$ is a bond, —O—, —S—, —$CH_2$—, —CH=CH—, —$CH_2$—$CH_2$—, amino or —$N(CH_3)$—, and $R^b$ is hydrogen, hydroxy, or $C_1$-$C_4$-alkyl optionally substituted by hydroxy;
$R^4$ is $C_1$-$C_4$-alkyl;
$R^5$ is $C_1$-alkyl substituted by —SO—$R^6$, —S(=O)$_2$—$R^6$, —CO—$R^6$, —CO—O—$R^6$, —CO—NH—$R^6$ or —$R^7$, or $R^5$ is $C_2$-$C_{10}$-alkyl substituted by —O—$R^6$, —S—$R^6$, —SO—$R^6$, —S(=O)$_2$—$R^6$, —CO—$R^6$, —O—CO—$R^6$, —CO—O—$R^6$, —NH—CO—$R^6$, —CO—NH—$R^6$, —$R^7$ or —$R^8$,
or $R^5$ is $C_2$-$C_{10}$-alkenyl or $C_2$-$C_{10}$-alkynyl optionally substituted by —$R^7$ or —$R^8$;
$R^6$ is a $C_3$-$C_{15}$-carbocyclic group or a 5- to 12-membered heterocyclic group having at least one ring heteroatom selected from nitrogen, oxygen and sulphur,
or $R^6$ is $C_1$-$C_{10}$-alkyl optionally substituted by $C_1$-$C_{10}$-alkoxy, —O—$R^7$, a $C_3$-$C_{15}$-carbocyclic group or a 5- to 12-membered heterocyclic group having at least one ring heteroatom selected from nitrogen, oxygen and sulphur;
$R^7$ is a 5- to 12-membered heterocyclic group having at least one ring heteroatom selected from nitrogen, oxygen and sulphur; and
$R^8$ is a $C_3$-$C_{15}$-carbocyclic group; or
L and M are (a bond and —$CH_2$—$CH_2$—), (—$CH_2$— and —$CH_2$—$CH_2$—) or (—$CH_2$—$CH_2$— and —$CH_2$—) respectively and J is $C_1$-$C_2$-alkylene,
or L and M are (—$CH_2$— and —$CH_2$—$CH_2$—) or (—$CH_2$—$CH_2$— and —$CH_2$—) respectively and J is a bond;
$R^1$ and $R^3$ are each independently a $C_3$-$C_{15}$-carbocyclic group or a 5- to 12-membered heterocyclic group having at least one ring heteroatom selected from nitrogen, oxygen and sulphur;
$R^2$ is hydrogen, hydroxy, or $C_1$-$C_4$-alkyl optionally substituted by hydroxy;
$R^4$ is $C_1$-$C_4$-alkyl;
$R^5$ is $C_1$-alkyl substituted by —CO—$R^9$, —CO—O—$R^9$ or —CO—NH—$R^9$,
or $R^5$ is $C_2$-$C_{10}$-alkyl substituted by $R^9$, —CO—$R^9$, —CO—O—$R^9$, —NH—CO—$R^9$ or —CO—NH—$R^9$, and
$R^9$ is a 5- to 12-membered heterocyclic group having at least one ring heteroatom selected from nitrogen, oxygen and sulphur.

Terms used in the specification have the following meanings:

"Optionally substituted" means the group referred to can be substituted at one or more positions, preferably one, two or three positions, by any one or any combination of the radicals described.

"Halo" or "halogen" as used herein denotes an element belonging to group 17 (formerly group VII) of the Periodic Table of Elements, which may be, for example, fluorine, chlorine, bromine or iodine.

"$C_1$-$C_{10}$-alkyl" as used herein denotes straight chain or branched alkyl having 1 to 10 carbon atoms.

"$C_1$-$C_2$-alkylene" as used herein denotes straight chain or branched alkylene having 1 or 2 carbon atoms.

"$C_2$-$C_{10}$-alkenyl" as used herein denotes straight chain or branched alkenyl having 2 to 10 carbon atoms.

"$C_2$-$C_{10}$-alkynyl" as used herein denotes straight chain or branched alkynyl having 2 to 10 carbon atoms.

"$C_1$-$C_{10}$-alkoxy" as used herein denotes straight chain or branched alkoxy having 1 to 10 carbon atoms.

"$C_3$-$C_{15}$-carbocyclic group" as used herein denotes a carbocyclic group having 3 to 15 ring carbon atoms, for example a monocyclic group, either cycloaliphatic, such as a $C_3$-$C_8$-cycloalkyl, for example cyclopentyl, cyclohexyl, cycloheptyl or cyclooctyl, or aromatic, such as phenyl, which can be substituted by one or more, usually one or two, $C_1$-$C_4$-alkyl groups, or a bicyclic group, such as a $C_8$-bicyclic, $C_9$-bicyclic or $C_{10}$-bicyclic group, which could be cycloaliphatic or could be aromatic, such as indanyl, indenyl or naphthyl, again any of which can be substituted by one or more, usually one or two, $C_1$-$C_4$-alkyl groups. The $C_3$-$C_{15}$-carbocyclic group can be substituted or unsubstituted.

"$C_3$-$C_8$-cycloalkyl" as used herein denotes cycloalkyl having 3 to 8 carbon atoms.

"$C_1$-$C_{10}$-haloalkyl" as used herein denotes $C_1$-$C_{10}$-alkyl as hereinbefore defined substituted by one or more halogen atoms, preferably one, two or three halogen atoms.

"$C_1$-$C_{10}$-alkylcarbonyl" as used herein denotes $C_1$-$C_{10}$-alkyl as hereinbefore defined linked to a carbonyl group.

"$C_1$-$C_{10}$-alkylsulfonyl" as used herein denotes $C_1$-$C_{10}$-alkyl as hereinbefore defined linked to —$SO_2$—.

"5- to 12-membered heterocyclic group containing at least one ring heteroatom selected from nitrogen, oxygen and sulphur" as used herein denotes a monoheterocyclic, biheterocyclic or triheterocyclic group, which may be saturated or unsaturated, that has 5 to 12 ring atoms. The 5- to 12-membered heterocyclic group can be unsubstituted or substituted, e.g. by one, two, three or four substituents.

"Aminocarbonyl" as used herein denotes amino attached through the nitrogen atom to a carbonyl group.

"$C_6$-$C_{10}$-aryl" as used herein denotes a monovalent carbocyclic aromatic group that contains 6 to 10 carbon atoms and which may be, for example, a monocyclic group such as phenyl or a bicyclic group such as naphthyl.

"$C_7$-$C_{15}$-aralkyl" as used herein denotes alkyl, for example $C_1$-$C_5$-alkyl as hereinbefore defined, substituted by $C_6$-$C_{10}$-aryl as hereinbefore defined.

In compounds of formula I the following are suitable or preferred aspects of the invention either independently or in any combination:

$R^2$ is preferably hydroxy. However when $R^2$ is $C_1$-$C_4$-alkyl, $R^2$ is preferably methyl or ethyl.

$R^b$ is preferably hydroxy. However when $R^b$ is $C_1$-$C_4$-alkyl, $R^b$ is preferably methyl or ethyl.

$R^4$ is preferably methyl.

$R^5$ is preferably $C_1$-alkyl substituted by —CO—NH—$R^6$, where $R^6$ is preferably a 5- or 6-membered heterocyclic group containing at least one ring heteroatom selected from nitrogen, oxygen and sulphur. However when $R^5$ is $C_2$-$C_{10}$-alkyl, $R^5$ is preferably $C_2$-$C_5$-alkyl, especially ethyl, propyl or butyl. When $R^5$ is $C_2$-$C_{10}$-alkenyl, $R^5$ is preferably $C_2$-$C_4$-alkenyl. And when $R^5$ is $C_2$-$C_{10}$-alkynyl, $R^5$ is preferably $C_2$-$C_8$-alkynyl, especially $C_2$-$C_4$-alkynyl.

$R^6$ is preferably a 5- or 6-membered heterocyclic group containing at least one ring heteroatom selected from nitrogen, oxygen and sulphur. However when $R^6$ is $C_1$-$C_{10}$-alkyl, $R^6$ is preferably $C_1$-$C_5$-alkyl, especially methyl or ethyl, and when $R^6$ is $C_1$-$C_{10}$-alkyl optionally substituted by $C_1$-$C_{10}$-alkoxy, $R^6$ is preferably $C_1$-$C_5$-alkyl substituted at one, two or three positions by $C_1$-$C_4$-alkoxy, especially methoxy or ethoxy.

When $R^1$ or $R^3$ is a $C_3$-$C_{15}$-carbocyclic group, $R^1$ or $R^3$ is preferably a $C_3$-$C_{10}$-carbocyclic group, for example $C_3$-$C_8$-cycloalkyl, phenyl, indanyl or naphthyl, but especially cyclopentyl, cyclohexyl or phenyl.

$R^1$ and $R^3$ are preferably unsubstituted $C_3$-$C_{15}$-carbocyclic groups. However when $R^1$ or $R^3$ is a $C_3$-$C_{15}$-carbocyclic group that is substituted it is preferably substituted at one, two or three positions by one or more of halo (especially fluoro), cyano, hydroxy, amino, nitro, carboxy, $C_1$-$C_{10}$-alkyl, $C_1$-$C_{10}$-haloalkyl, $C_1$-$C_{10}$-alkoxy, $C_1$-$C_{10}$-alkylcarbonyl, $C_1$-$C_{10}$-alkyl-sulfonyl, —$SO_2NH_2$, —COO—$C_6$-$C_{10}$-aryl, —COO—$C_7$-$C_{15}$-aralkyl, a $C_3$-$C_{15}$-carbocyclic group and a 5- to 12-membered heterocyclic group having at least one ring heteroatom selected from nitrogen, oxygen and sulphur.

When either $R^6$ or $R^8$ is a $C_3$-$C_{15}$-carbocyclic group, it is preferably a $C_3$-$C_{10}$-carbocyclic group, for example $C_3$-$C_8$-cycloalkyl, phenyl, indanyl or naphthyl, but especially phenyl.

$R^6$ and $R^8$ are preferably unsubstituted $C_3$-$C_{15}$-carbocyclic groups. However when either $R^6$ or $R^8$ is a $C_3$-$C_{15}$-carbocyclic group that is substituted it is preferably substituted at one, two or three positions by one or more of halo (especially fluoro), cyano, hydroxy, amino, nitro, carboxy, $C_1$-$C_{10}$-alkyl, $C_1$-$C_{10}$-haloalkyl, $C_1$-$C_{10}$-alkoxy, $C_1$-$C_{10}$-alkylcarbonyl, $C_1$-$C_{10}$-alkyl-sulfonyl, —$SO_2NH_2$, —COO—$C_6$-$C_{10}$-aryl, —COO—$C_7$-$C_{15}$-aralkyl, a $C_3$-$C_{15}$-carbocyclic group and a 5- to 12-membered heterocyclic group having at least one ring heteroatom selected from nitrogen, oxygen and sulphur.

When either $R^1$, $R^3$, $R^6$ or $R^5$ is a $C_3$-$C_{15}$-carbocyclic group that is substituted it is preferably substituted at one, two or three positions by unsubstituted phenyl.

When either $R^1$, $R^3$, $R^6$ or $R^8$ is a $C_3$-$C_5$-carbocyclic group that is substituted by halo it is preferably substituted at one, two or three positions by fluorine, chlorine or bromine.

When either $R^1$, $R^3$, $R^6$ or $R^8$ is a $C_3$-$C_{15}$-carbocyclic group that is substituted by $C_1$-$C_{10}$-haloalkyl, it is preferably substituted at one, two or three positions by $C_1$-$C_4$-haloalkyl.

When either $R^1$, $R^3$, $R^6$ or $R^8$ is a $C_3$-$C_{15}$-carbocyclic group that is substituted by $C_1$-$C_{10}$-alkylcarbonyl, it is preferably substituted at one, two or three positions by $C_1$-$C_4$-alkylcarbonyl.

When either $R^1$, $R^3$, $R^6$ or $R^8$ is a $C_3$-$C_{15}$-carbocyclic group that is substituted by $C_1$-$C_{10}$-alkyl-sulfonyl, it is preferably substituted at one, two or three positions by $C_1$-$C_4$-alkylsulfonyl.

When either $R^1$, $R^3$, $R^6$ or $R^8$ is a $C_3$-$C_{15}$-carbocyclic group that is substituted by —COO—$C_6$-$C_{10}$-aryl, it is preferably substituted at one, two or three positions by —COO—$C_6$-$C_8$-aryl, especially —COO-phenyl.

When either $R^1$, $R^3$, $R^6$ or $R^8$ a $C_3$-$C_{15}$-carbocyclic group that is substituted by —COO—$C_7$-$C_{15}$-aralkyl, it is preferably substituted at one, two or three positions by —COO—$C_7$-$C_{10}$-aralkyl, especially —COO—$C_1$-$C_4$-alkyl-phenyl.

When $R^1$ or $R^3$ is a 5- to 12-membered heterocyclic group containing at least one ring heteroatom selected from nitrogen, oxygen and sulphur, $R^1$ or $R^3$ is preferably a 5- to 9-membered heterocyclic group, which can be a monoheterocyclic group such as furyl, pyrrolyl, pyrrolidinyl, pyrazolyl, imidazolyl, triazolyl, tetrazolyl, thienyl, thiadiazolyl, isothiazolyl, oxadiazolyl, pyridinyl, oxazolyl, isoxazolyl, piperidinyl, pyridinyl, pyrazinyl, pyridazinyl, pyrimidinyl, piperazinyl, morpholinyl, triazinyl, oxazinyl or thiazolyl, or a biheterocyclic group such as benzazolyl, benzimidazolyl, indazolyl and benzothiazolyl. When $R^1$ or $R^3$ is a 5- to 9-membered heterocyclic group it is preferably furyl, pyrrolyl, triazolyl, thienyl, thiadiazolyl, oxazolyl, isoxazolyl, piperidinyl, pyridinyl, pyrazinyl, benzazolyl, benzimidazolyl, indazolyl or benzothiazolyl, but especially thienyl. The 5- to 12-membered heterocyclic group can be unsubstituted or substituted, e.g. by one, two, three or four substituents selected from halo, cyano, oxo, hydroxy, carboxy, nitro, $C_1$-$C_{10}$-alkyl, $C_1$-$C_{10}$-alkylcarbonyl and $C_1$-$C_{10}$-alkoxy optionally substituted by aminocarbonyl. However when $R^1$ or $R^3$ is a 5- to 12-membered heterocyclic group it is especially unsubstituted thienyl.

When $R^6$ or $R^9$ is a 5- to 12-membered heterocyclic group containing at least one ring heteroatom selected from nitrogen, oxygen and sulphur, it is preferably a 5- to 9-membered heterocyclic group, which can be a monoheterocyclic group such as furyl, pyrrolyl, pyrrolidinyl, pyrazolyl, imidazolyl, triazolyl, tetrazolyl, thienyl, thiadiazolyl, isothiazolyl, oxadiazolyl, pyridinyl, oxazolyl, isoxazolyl, piperidinyl, pyridinyl, pyrazinyl, pyridazinyl, pyrimidinyl, piperazinyl, morpholinyl, triazinyl, oxazinyl or thiazolyl, or a biheterocyclic group such as benzazolyl, benzimidazolyl, indazolyl and benzothiazolyl. When $R^6$ or $R^9$ is a 5- to 9-membered heterocyclic group it is preferably furyl, pyrrolyl, triazolyl, thienyl, thiadiazolyl, oxazolyl, isoxazolyl, piperidinyl, pyridinyl, pyrazinyl, benzazolyl, benzimidazolyl, indazolyl or benzothiazolyl, but especially thienyl. The 5- to 12-membered heterocyclic group can be unsubstituted or substituted, e.g. by one, two, three or four substituents selected from halo, cyano, oxo, hydroxy, carboxy, nitro, $C_1$-$C_{10}$-alkyl, $C_1$-$C_{10}$-alkylcarbonyl and $C_1$-$C_{10}$-alkoxy optionally substituted by aminocarbonyl. However when $R^6$ or $R^9$ is a 5- to 12-membered heterocyclic group it is most preferably isoxazolyl, pyrazinyl, triazinyl, pyrimidinyl, pyridinyl, pyridazinyl, in particular isoxazol-3-yl, pyrazin-2-yl, [1,3,5]triazin-2-yl, pyrimidin-2-yl, pyrimidin-4-yl, pyrimidin-5-yl, pyridin-2-yl, pyridin-3-yl, pyridin-4-yl or pyridazin-3-yl.

When $R^7$ is a 5- to 12-membered heterocyclic group containing at least one ring heteroatom selected from nitrogen, oxygen and sulphur, it is preferably a 5- to 9-membered heterocyclic group, which can be a monoheterocyclic group such as furyl, pyrrolyl, pyrrolidinyl, pyrazolyl, imidazolyl, triazolyl, tetrazolyl, thienyl, thiadiazolyl, isothiazolyl, oxadiazolyl, pyridinyl, oxazolyl, isoxazolyl, piperidinyl, pyridinyl, pyrazinyl, pyridazinyl, pyrimidinyl, piperazinyl, morpholinyl, triazinyl, oxazinyl or thiazolyl, or a biheterocyclic group such as benzazolyl, benzimidazolyl, indazolyl and benzothiazolyl. When $R^7$ is a 5- to 9-membered heterocyclic group it is preferably furyl, pyrrolyl, triazolyl, thienyl, thiadiazolyl, oxazolyl, isoxazolyl, piperidinyl, pyridinyl, pyrazinyl, benzazolyl, benzimidazolyl, indazolyl or benzothiazolyl, but especially thienyl. The 5- to 12-membered heterocyclic group can be unsubstituted or substituted, e.g. by one, two, three or four substituents selected from halo, cyano, oxo, hydroxy, carboxy, nitro, $C_1$-$C_{10}$-alkyl, $C_1$-$C_{10}$-alkylcarbonyl and $C_1$-$C_{10}$-alkoxy optionally substituted by aminocarbonyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds include those of formula I in salt or zwitterionic form wherein
L and M are (a bond and —CH$_2$—CH$_2$—) and J is $C_1$-$C_2$-alkylene,
or L and M are (—CH$_2$— and —CH$_2$—CH$_2$—) or (—CH$_2$—CH$_2$— and —CH$_2$—) respectively and J is a bond;
$R^1$ is a $C_3$-$C_{15}$-carbocyclic group or a 5- to 12-membered heterocyclic group having at least one ring heteroatom selected from nitrogen, oxygen and sulphur;
$R^2$ is hydroxy;
$R^3$ is a $C_3$-$C_{15}$-carbocyclic group or a 5- to 12-membered heterocyclic group having at least one ring heteroatom selected from nitrogen, oxygen and sulphur,
wherein $R^1$ and $R^3$ are not the same;
or —CR$^1$R$^2$R$^3$ together form a group of formula

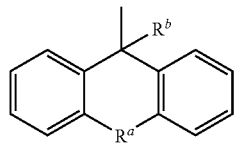

where $R^a$ is a bond, and $R^b$ is hydroxy;
$R^4$ is methyl;
$R^5$ is $C_1$-alkyl substituted by —CO—NH—R$^6$,
or $R^5$ is $C_2$-$C_{10}$-alkyl substituted by —O—R$^6$ or —R$^8$;
$R^6$ is a $C_3$-$C_{15}$-carbocyclic group or a 5- to 12-membered heterocyclic group having at least one ring heteroatom selected from nitrogen, oxygen and sulphur; and
$R^8$ is a $C_3$-$C_{15}$-carbocyclic group; or
L and M are a bond and —CH$_2$—CH$_2$— respectively and J is $C_1$-$C_2$-alkylene,
or L and M are (—CH$_2$— and —CH$_2$—CH$_2$—) or (—CH$_2$—CH$_2$— and —CH$_2$—) respectively and J is a bond;
$R^1$ and $R^3$ are both $C_3$-$C_{15}$-carbocyclic groups;
$R^2$ is hydroxy;
$R^4$ is methyl;
$R^5$ is $C_1$-alkyl substituted by —CO—NH—R$^9$; and
$R^9$ is a 5- to 12-membered heterocyclic group having at least one ring heteroatom selected from nitrogen, oxygen and sulphur.

Especially preferred compounds include those of formula I in salt or zwitterionic form wherein L and M are (a bond and —CH$_2$—CH$_2$—) and J is $C_1$-$C_2$-alkylene,
or L and M are (—CH$_2$— and —CH$_2$—CH$_2$—) or (—CH$_2$—CH$_2$— and —CH$_2$—) respectively and J is a bond;
$R^1$ is a $C_3$-$C_{10}$-carbocyclic group, or a 5- to 9-membered heterocyclic group having at least one ring heteroatom selected from nitrogen, oxygen and sulphur;
$R^2$ is hydroxy;
$R^3$ is a $C_3$-$C_{10}$-carbocyclic group, preferably phenyl or $C_3$-$C_6$-cycloalkyl, or a 5- to 9-membered heterocyclic group having at least one ring heteroatom selected from nitrogen, oxygen and sulphur,
wherein $R^1$ and $R^3$ are not the same;
or —CR$^1$R$^2$R$^3$ together form a group of formula

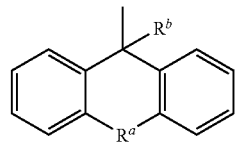

where $R^a$ is a bond, and $R^b$ is hydroxy;
$R^4$ is methyl;
$R^5$ is $C_1$-alkyl substituted by —CO—NH—R$^6$,
or $R^5$ is $C_2$-$C_4$-alkyl substituted by —O—R$^6$ or —R$^8$;
$R^6$ is a $C_3$-$C_{10}$-carbocyclic group, preferably phenyl, or a 5- to 9-membered heterocyclic group having at least one ring heteroatom selected from nitrogen, oxygen and sulphur; and
$R^8$ is a $C_3$-$C_{10}$-carbocyclic group, preferably phenyl; or
L and M are a bond and —CH$_2$—CH$_2$— respectively and J is $C_1$-$C_2$-alkylene,
or L and M are (—CH$_2$— and —CH$_2$—CH$_2$—) or (—CH$_2$—CH$_2$— and —CH$_2$—) respectively and J is a bond;
$R^1$ and $R^3$ are both $C_3$-$C_{10}$-carbocyclic groups, preferably phenyl;
$R^2$ is hydroxy;
$R^4$ is methyl;
$R^5$ is $C_1$-alkyl substituted by —CO—NH—R$^9$; and
$R^9$ is a 5- to 9-membered heterocyclic group having at least one ring heteroatom selected from nitrogen, oxygen and sulphur, preferably isoxazolyl, pyrazinyl or triazinyl.

The compounds of formula I are quaternary ammonium salts. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic e.g. carboxyl groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

The compounds of the invention include at least one chiral centre and therefore the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof. Particularly preferred compounds of in invention are single isomers, either single enantiomers or single diastereoisomers. Surprisingly these single isomers allow the most potent component of a mixture to be selected and surprisingly can offer improved residency times at the M3 receptor hence delivering agents with long duration of action which are particularly suitable for once-daily dosing.

Specific especially preferred compounds of the invention are those described hereinafter in the Examples.

Examples of specific preferred compounds of formula I in salt or zwitterionic form also include:

(R)-3-(2-Hydroxy-2,2-diphenyl-acetoxy)-1-methyl-1-(3-pyrazin-2-yl-propyl)-piperidinium;
(R)-3-(2-Hydroxy-2,2-diphenyl-acetoxy)-1-methyl-1-(3-pyrimidinyl-propyl)-piperidinium;
(R)-3-(2-Hydroxy-2,2-diphenyl-acetoxy)-1-methyl-1-(3-pyrimidin-2-yl-propyl)-piperidinium;
(R)-3-(2-Hydroxy-2,2-diphenyl-acetoxy)-1-methyl-1-(3-pyrimidin-5-yl-propyl)-piperidinium;
(R)-3-(2-Hydroxy-2,2-diphenyl-acetoxy)-1-methyl-1-(3-pyridin-2-yl-propyl)-piperidinium;
(R)-3-(2-Hydroxy-2,2-diphenyl-acetoxy)-1-methyl-1-(3-pyridin-4-yl-propyl)-piperidinium;
(R)-3-(2-Hydroxy-2,2-diphenyl-acetoxy)-1-methyl-1-(3-pyridin-3-yl-propyl)-piperidinium;
(R)-3-(2-Hydroxy-2,2-diphenyl-acetoxy)-1-(3-isoxazol-3-yl-propyl)-1-methyl-piperidinium;
(R)-3-(2-Hydroxy-2,2-diphenyl-acetoxy)-1-methyl-1-(2-pyrazin-2-yl-ethyl)-piperidinium;
(R)-3-(2-Hydroxy-2,2-diphenyl-acetoxy)-1-methyl-1-(2-pyrimidin-4-yl-ethyl)-piperidinium;
(R)-3-(2-Hydroxy-2,2-diphenyl-acetoxy)-1-methyl-1-(2-pyrimidin-2-yl-ethyl)-piperidinium;
(R)-3-(2-Hydroxy-2,2-diphenyl-acetoxy)-1-methyl-1-(2-pyrimidin-5-yl-ethyl)-piperidinium;
(R)-3-(2-Hydroxy-2,2-diphenyl-acetoxy)-1-methyl-1-(2-pyridin-2-yl-ethyl)-piperidinium;
(R)-3-(2-Hydroxy-2,2-diphenyl-acetoxy)-1-methyl-1-(2-pyridin-4-yl-ethyl)-piperidinium;
(R)-3-(2-Hydroxy-2,2-diphenyl-acetoxy)-1-methyl-1-(2-pyridin-3-yl-ethyl)-piperidinium;
(R)-3-(2-Hydroxy-2,2-diphenyl-acetoxy)-1-(2-isoxazol-3-yl-ethyl)-1-methyl-piperidinium;
(R)-3-(2-Hydroxy-2,2-diphenyl-acetoxy)-1-methyl-1-[(5-methyl-isoxazol-3-ylcarbamoyl)-methyl]-piperidinium;
(R)-3-(2-Hydroxy-2,2-diphenyl-acetoxy)-1-methyl-1-(pyridazin-2-ylcarbamoylmethyl)-piperidinium;
(R)-3-(2-Hydroxy-2,2-diphenyl-acetoxy)-1-methyl-1-(pyridazin-3-ylcarbamoylmethyl)-piperidinium;
(R)-3-(2-Hydroxy-2,2-diphenyl-acetoxy)-1-methyl-1-([1,3,5]triazin-2-ylcarbamoylmethyl)-piperidinium;
(R)-3-(2-Hydroxy-2,2-diphenyl-acetoxy)-1-methyl-1-(pyrimidin-4-ylcarbamoylmethyl)-piperidinium;
(R)-3-(2-Cyclopentyl-2-hydroxy-2-phenyl-acetoxy)-1-methyl-1-(3-phenyl-propyl)-piperidinium
(R)-3-(2-Cyclopentyl-2-hydroxy-2-phenyl-acetoxy)-1-methyl-1-(3-pyrazin-2-yl-propyl)-piperidinium;
(R)-3-(2-Cyclopentyl-2-hydroxy-2-phenyl-acetoxy)-1-methyl-1-(3-pyridin-4-yl-propyl)-piperidinium;
(R)-3-(2-Cyclopentyl-2-hydroxy-2-phenyl-acetoxy)-1-methyl-1-(3-pyrimidin-2-yl-propyl)-piperidinium;
(R)-3-(2-Cyclopentyl-2-hydroxy-2-phenyl-acetoxy)-1-methyl-1-(3-pyrimidin-5-yl-propyl)-piperidinium;
(R)-3-(2-Cyclopentyl-2-hydroxy-2-phenyl-acetoxy)-1-methyl-1-(3-pyridin-2-yl-propyl)-piperidinium;
(R)-3-(2-Cyclopentyl-2-hydroxy-2-phenyl-acetoxy)-1-methyl-1-(3-pyridin-4-yl-propyl)-piperidinium;
(R)-3-(2-Cyclopentyl-2-hydroxy-2-phenyl-acetoxy)-1-(3-isoxazol-3-yl-propyl)-1-methyl-piperidinium;
(R)-3-(2-Cyclopentyl-2-hydroxy-2-phenyl-acetoxy)-1-methyl-1-phenethyl-piperidinium;
(R)-3-(2-Cyclopentyl-2-hydroxy-2-phenyl-acetoxy)-1-methyl-1-(2-pyrazin-2-yl-ethyl)-piperidinium;
(R)-3-(2-Cyclopentyl-2-hydroxy-2-phenyl-acetoxy)-1-methyl-1-(2-pyrimidin-4-yl-ethyl)-piperidinium;
(R)-3-(2-Cyclopentyl-2-hydroxy-2-phenyl-acetoxy)-1-methyl-1-(2-pyrimidin-2-yl-ethyl)-piperidinium;
(R)-3-(2-Cyclopentyl-2-hydroxy-2-phenyl-acetoxy)-1-methyl-1-(2-pyrimidin-5-yl-ethyl)-piperidinium;
(R)-3-(2-Cyclopentyl-2-hydroxy-2-phenyl-acetoxy)-1-methyl-1-(2-pyridin-2-yl-ethyl)-piperidinium;
(R)-3-(2-Cyclopentyl-2-hydroxy-2-phenyl-acetoxy)-1-methyl-1-(2-pyridin-4-yl-ethyl)-piperidinium;
(R)-3-(2-Cyclopentyl-2-hydroxy-2-phenyl-acetoxy)-1-methyl-1-(2-pyridin-3-yl-ethyl)-piperidinium;
(R)-3-(2-Cyclopentyl-2-hydroxy-2-phenyl-acetoxy)-1-(2-isoxazol-3-yl-ethyl)-1-methyl-piperidinium;
(R)-3-(2-Cyclopentyl-2-hydroxy-2-phenyl-acetoxy)-1-methyl-1-[(5-methyl-isoxazol-3-ylcarbamoyl)-methyl]-piperidinium;
(R)-3-(2-Cyclopentyl-2-hydroxy-2-phenyl-acetoxy)-1-methyl-1-(pyrazin-2-ylcarbamoylmethyl)-piperidinium;
(R)-3-(2-Cyclopentyl-2-hydroxy-2-phenyl-acetoxy)-1-methyl-1-(pyridazin-3-ylcarbamoyl-methyl)-piperidinium;
(R)-3-(2-Cyclopentyl-2-hydroxy-2-phenyl-acetoxy)-1-methyl-1-([1,3,5]triazin-2-ylcarbamoyl-methyl)-piperidinium;
(R)-3-(2-Cyclopentyl-2-hydroxy-2-phenyl-acetoxy)-1-methyl-1-(pyrimidinylcarbamoyl-methyl)-piperidinium;
(R)-3-(2-Cyclohexyl-2-hydroxy-2-phenyl-acetoxy)-1-methyl-1-(3-phenyl-propyl)-piperidinium;
(R)-3-(2-Cyclohexyl-2-hydroxy-2-phenyl-acetoxy)-1-methyl-1-(3-pyrazin-2-yl-propyl)-piperidinium;
(R)-3-(2-Cyclohexyl-2-hydroxy-2-phenyl-acetoxy)-1-methyl-1-(3-pyrimidin-4-yl-propyl)-piperidinium;
(R)-3-(2-Cyclohexyl-2-hydroxy-2-phenyl-acetoxy)-1-methyl-1-(3-pyrimidin-2-yl-propyl)-piperidinium;
(R)-3-(2-Cyclohexyl-2-hydroxy-2-phenyl-acetoxy)-1-methyl-1-(3-pyrimidin-5-yl-propyl)-piperidinium;

(R)-3-(2-Cyclohexyl-2-hydroxy-2-phenyl-acetoxy)-1-methyl-1-(3-pyridin-2-yl-propyl)-piperidinium;
(R)-3-(2-Cyclohexyl-2-hydroxy-2-phenyl-acetoxy)-1-methyl-1-(3-pyridin-4-yl-propyl) piperidinium;
(R)-3-(2-Cyclohexyl-2-hydroxy-2-phenyl-acetoxy)-1-methyl-1-(3-pyridin-3-yl-propyl)-piperidinium;
(R)-3-(2-Cyclohexyl-2-hydroxy-2-phenyl-acetoxy)-1-(3-isoxazol-3-yl-propyl)-1-methyl-piperidinium;
(R)-3-(2-Cyclohexyl-2-hydroxy-2-phenyl-acetoxy)-1-methyl-1-phenethyl-piperidinium;
(R)-3-(2-Cyclohexyl-2-hydroxy-2-phenyl-acetoxy)-1-methyl-1-(2-pyrazin-2-yl-ethyl)-piperidinium;
(R)-3-(2-Cyclohexyl-2-hydroxy-2-phenyl-acetoxy)-1-methyl-1-(2-pyrimidin-4-yl-ethyl)-piperidinium;
(R)-3-(2-Cyclohexyl-2-hydroxy-2-phenyl-acetoxy)-1-methyl-1-(2-pyrimidin-2-yl-ethyl)-piperidinium;
(R)-3-(2-Cyclohexyl-2-hydroxy-2-phenyl-acetoxy)-1-methyl-1-(2-pyrimidin-5-yl-ethyl)-piperidinium;
(R)-3-(2-Cyclohexyl-2-hydroxy-2-phenyl-acetoxy)-1-methyl-1-(2-pyridin-2-yl-ethyl)-piperidinium;
(R)-3-(2-Cyclohexyl-2-hydroxy-2-phenyl-acetoxy)-1-methyl-1-(2-pyridin-4-yl-ethyl)-piperidinium;
(R)-3-(2-Cyclohexyl-2-hydroxy-2-phenyl-acetoxy)-1-methyl-1-(2-pyridin-3-yl-ethyl)-piperidinium;
(R)-3-(2-Cyclohexyl-2-hydroxy-2-phenyl-acetoxy)-1-(2-isoxazol-3-yl-ethyl)-1-methyl-piperidinium;
(R)-3-(2-Cyclohexyl-2-hydroxy-2-phenyl-acetoxy)-1-methyl-1-[(5-methyl-isoxazol-3-ylcarbamoyl)-methyl]-piperidinium;
(R)-3-(2-Cyclohexyl-2-hydroxy-2-phenyl-acetoxy)-1-methyl-1-(pyrazin-2-ylcarbamoylmethyl)-piperidinium;
(R)-3-(2-Cyclohexyl-2-hydroxy-2-phenyl-acetoxy)-1'-methyl-1'-(pyridazin-3-ylcarbamoyl-methyl)-piperidinium;
(R)-3-(2-Cyclohexyl-2-hydroxy-2-phenyl-acetoxy)-1-methyl-1-([1,3,5]triazin-2-ylcarbamoyl-methyl)-piperidinium;
(R)-3-(2-Cyclohexyl-2-hydroxy-2-phenyl-acetoxy)-1-methyl-1-(pyrimidinylcarbamoyl-methyl)-piperidinium;
(R)-3-(9-Hydroxy-9H-fluorene-9-carbonyloxy)-1-methyl-1-(3-phenyl-propyl)-piperidinium;
(R)-3-(9-Hydroxy-9H-fluorene-9-carbonyloxy)-1-methyl-1-(3-pyrazin-2-yl-propyl)-piperidinium;
(R)-3-(9-Hydroxy-9H-fluorene-9-carbonyloxy)-1-methyl-1-(3-pyrimidin-4-yl-propyl)piperidinium;
(R)-3-(9-Hydroxy-9H-fluorene-9-carbonyloxy)-1-methyl-1-(3-pyrimidin-2-yl-propyl)-piperidinium;
(R)-3-(9-Hydroxy-9H-fluorene-9-carbonyloxy)-1-methyl-1-(3-pyrimidin-5-yl-propyl)-piperidinium;
(R)-3-(9-Hydroxy-9H-fluorene-9-carbonyloxy)-1-methyl-1-(3-pyridin-2-yl-propyl)-piperidinium;
(R)-3-(9-Hydroxy-9H-fluorene-9-carbonyloxy)-1-methyl-1-(3-pyridin-4-yl-propyl)-piperidinium;
(R)-3-(9-Hydroxy-9H-fluorene-9-carbonyloxy)-1-methyl-1-(3-pyridin-3-yl-propyl)-piperidinium;
(R)-3-(9-Hydroxy-9H-fluorene-9-carbonyloxy)-1-(3-isoxazol-3-yl-propyl)-1-methyl-piperidinium;
(R)-3-(9-Hydroxy-9H-fluorene-9-carbonyloxy)-1-methyl-1-phenethyl-piperidinium;
(R)-3-(9-Hydroxy-9H-fluorene-9-carbonyloxy)-1-methyl-1-(2-pyrazin-2-yl-ethyl)-piperidinium;
(R)-3-(9-Hydroxy-9H-fluorene-9-carbonyloxy)-1-methyl-1-(2-pyrimidin-4-yl-ethyl)-piperidinium;
(R)-3-(9-Hydroxy-9H-fluorene-9-carbonyloxy)-1-methyl-1-(2-pyrimidin-2-yl-ethyl)-piperidinium;
(R)-3-(9-Hydroxy-9H-fluorene-9-carbonyloxy)-1-methyl-1-(2-pyrimidin-5-yl-ethyl)-piperidinium;
(R)-3-(9-Hydroxy-9H-fluorene-9-carbonyloxy)-1-methyl-1-(2-pyridin-2-yl-ethyl)-piperidinium;
(R)-3-(9-Hydroxy-9H-fluorene-9-carbonyloxy)-1-methyl-1-(2-pyridin-4-yl-ethyl)-piperidinium;
(R)-3-(9-Hydroxy-9H-fluorene-9-carbonyloxy)-1-methyl-1-(2-pyridin-3-yl-ethyl)-piperidinium;
(R)-3-(9-Hydroxy-9H-fluorene-9-carbonyloxy)-1-(2-isoxazol-3-yl-ethyl)-1-methyl-piperidinium;
(R)-3-(9-Hydroxy-9H-fluorene-9-carbonyloxy)-1-methyl-1-[(5-methyl-isoxazol-3-ylcarbamoyl)-methyl]-piperidinium;
(R)-3-(9-Hydroxy-9H-fluorene-9-carbonyloxy)-1-methyl-1-(pyrazin-2-ylcarbamoylmethyl)-piperidinium;
(R)-3-(9-Hydroxy-9H-fluorene-9-carbonyloxy)-1-methyl-1-(pyridazin-3-ylcarbamoylmethyl)-piperidinium;
(R)-3-(9-Hydroxy-9H-fluorene-9-carbonyloxy)-1-methyl-1-([1,3,5]triazin-2-ylcarbamoyl-methyl)-piperidinium;
(R)-3-(9-Hydroxy-9H-fluorene-9-carbonyloxyl)-1-methyl-1-(pyrimidin-4-ylcarbamoylmethyl)-piperidinium;
4-(2-Hydroxy-2,2-diphenyl-acetoxy)-1-methyl-1-(3-pyrazin-2-yl-propyl)-piperidinium;
4-(2-Hydroxy-2,2-diphenyl-acetoxy)-1-methyl-1-(3-pyrimidin-4-yl-propyl)-piperidinium;
4-(2-Hydroxy-2,2-diphenyl-acetoxy)-1-methyl-1-(3-pyrimidin-2-yl-propyl)-piperidinium;
4-(2-Hydroxy-2,2-diphenyl-acetoxy)-1-methyl-1-(3-pyrimidin-5-yl-propyl)-piperidinium;
4-(2-Hydroxy-2,2-diphenyl-acetoxy)-1-methyl-1-(3-pyridin-2-yl-propyl)-piperidinium;
4-(2-Hydroxy-2,2-diphenyl-acetoxy)-1-methyl-1-(3-pyridin-4-yl-propyl)-piperidinium;
4-(2-Hydroxy-2,2-diphenyl-acetoxy)-1-methyl-1-(3-pyridin-3-yl-propyl)-piperidinium;
4-(2-Hydroxy-2,2-diphenyl-acetoxy)-1-methyl-1-(3-isoxazol-3-yl-propyl)-1-methyl-piperidinium;
4-(2-Hydroxy-2,2-diphenyl-acetoxy)-1-methyl-1-(2-pyrazin-2-yl-ethyl)-piperidinium;
4-(2-Hydroxy-2,2-diphenyl-acetoxy)-1-methyl-1-(2-pyrimidin-4-yl-ethyl)-piperidinium;
4-(2-Hydroxy-2,2-diphenyl-acetoxy)-1-methyl-1-(2-pyrimidin-2-yl-ethyl)-piperidinium;
4-(2-Hydroxy-2,2-diphenyl-acetoxy)-1-methyl-1-(2-pyrimidin-5-yl-ethyl)-piperidinium;
4-(2-Hydroxy-2,2-diphenyl-acetoxy)-1-methyl-1-(2-pyridin-2-yl-ethyl)-piperidinium;
4-(2-Hydroxy-2,2-diphenyl-acetoxy)-1-methyl-1-(2-pyridin-4-yl-ethyl)-piperidinium;
4-(2-Hydroxy-2,2-diphenyl-acetoxy)-1-methyl-1-(2-pyridin-3-yl-ethyl)-piperidinium; 4-(2-Hydroxy-2,2-diphenyl-acetoxy)-1-(2-isoxazol-3-yl-ethyl)-1-methyl-piperidinium;
4-(2-Hydroxy-2,2-diphenyl-acetoxy)-1-methyl-1-[(5-methyl-isoxazol-3-ylcarbamoyl)-methyl]-piperidinium;
4-(2-Hydroxy-2,2-diphenyl-acetoxy)-1-methyl-1-(pyridazin-3-ylcarbamoylmethyl)-piperidinium;
4-(2-Hydroxy-2,2-diphenyl-acetoxy)-1-methyl-1-([1,3,5]triazin-2-ylcarbamoylmethyl)-piperidinium;
4-(2-Hydroxy-2,2-diphenyl-acetoxy)-1-methyl-1-(pyrimidin-4-ylcarbamoylmethyl)-piperidinium;
4-(2-Cyclopentyl-2-hydroxy-2-phenyl-acetoxy)-1-methyl-1-(3-phenyl-propyl)-piperidinium;
4-(2-Cyclopentyl-2-hydroxy-2-phenyl-acetoxy)-1-methyl-1-(3-pyrazin-2-yl-propyl)-piperidinium;
4-(2-Cyclopentyl-2-hydroxy-2-phenyl-acetoxy)-1-methyl-1-(3-pyrimidin-4-yl-propyl)-piperidinium;
4-(2-Cyclopentyl-2-hydroxy-2-phenyl-acetoxy)-1-methyl-1-(3-pyrimidin-2-yl-propyl)-piperidinium;

4-(2-Cyclopentyl-2-hydroxy-2-phenyl-acetoxy)-1-methyl-1-(3-pyrimidin-5-yl-propyl)-piperidinium;
4-(2-Cyclopentyl-2-hydroxy-2-phenyl-acetoxy)-1-methyl-1'-(3-pyridin-2-yl-propyl)-piperidinium;
4-(2-Cyclopentyl-2-hydroxy-2-phenyl-acetoxy)-1-methyl-1-(3-pyridin-2-yl-propyl)-piperidinium;
4-(2-Cyclopentyl-2-hydroxy-2-phenyl-acetoxy)-1-methyl-1-(3-pyridin-3-yl-propyl)-piperidinium;
4-(2-Cyclopentyl-2-hydroxy-2-phenyl-acetoxy)-1-(3-isoxazol-3-yl-propyl)-1-methyl-piperidinium;
4-(2-Cyclopentyl-2-hydroxy-2-phenyl-acetoxy)-1-methyl-1-phenethyl-piperidinium;
4-(2-Cyclopentyl-2-hydroxy-2-phenyl-acetoxy)-1-methyl-1-(2-pyrazin-2-yl-ethyl)-piperidinium;
4-(2-Cyclopentyl-2-hydroxy-2-phenyl-acetoxy)-1-methyl-1-(2-pyrimidin-4-yl-ethyl)-piperidinium;
4-(2-Cyclopentyl-2-hydroxy-2-phenyl-acetoxy)-1-methyl-1-(2-pyrimidin-2-yl-ethyl)-piperidinium;
4-(2-Cyclopentyl-2-hydroxy-2-phenyl-acetoxy)-1-methyl-1-(2-pyrimidin-5-yl-ethyl)-piperidinium;
4-(2-Cyclopentyl-2-hydroxy-2-phenyl-acetoxy)-1-methyl-1-(2-pyridin-2-yl-ethyl)-piperidinium;
4-(2-Cyclopentyl-2-hydroxy-2-phenyl-acetoxy)-1-methyl-1-(2-pyridin-4-yl-ethyl)-piperidinium;
4-(2-Cyclopentyl-2-hydroxy-2-phenyl-acetoxy)-1-methyl-1-(2-pyridin-3-yl-ethyl)-piperidinium;
4-(2-Cyclopentyl-2-hydroxy-2-phenyl-acetoxy)-1-(2-isoxazol-3-yl-ethyl)-1-methyl-piperidinium;
4-(2-Cyclopentyl-2-hydroxy-2-phenyl-acetoxy)-1-methyl-1-[(5-methyl-isoxazol-3-ylcarbamoyl)-methyl]-piperidinium;
4-(2-Cyclopentyl-2-hydroxy-2-phenyl-acetoxy)-1-methyl-1-(pyridazin-3-ylcarbamoylmethyl)-piperidinium;
4-(2-Cyclopentyl-2-hydroxy-2-phenyl-acetoxy)-1-methyl-1-([1,3,5]triazin-2-ylcarbamoyl-methyl)-piperidinium;
4-(2-Cyclopentyl-2-hydroxy-2-phenyl-acetoxy)-1-methyl-1-(pyrimidin-4-ylcarbamoylmethyl)-piperidinium;
4-(2-Cyclohexyl-2-hydroxy-2-phenyl-acetoxy)-1-methyl-1-(3-phenyl-propyl)-piperidinium;
4-(2-Cyclohexyl-2-hydroxy-2-phenyl-acetoxy)-1-methyl-1-(3-pyrazin-2-yl-propyl)-piperidinium;
4-(2-Cyclohexyl-2-hydroxy-2-phenyl-acetoxy)-1-methyl-1-(3-pyrimidin-4-yl-propyl)-piperidinium;
4-(2-Cyclohexyl-2-hydroxy-2-phenyl-acetoxy)-1-methyl-1-(3-pyrimidin-2-yl-propyl)-piperidinium;
4-(2-Cyclohexyl-2-hydroxy-2-phenyl-acetoxy)-1-methyl-1-(3-pyrimidin-5-yl-propyl)-piperidinium;
4-(2-Cyclohexyl-2-hydroxy-2-phenyl-acetoxy)-1-methyl-1-(3-pyridin-2-yl-propyl)-piperidinium;
4-(2-Cyclohexyl-2-hydroxy-2-phenyl-acetoxy)-1-methyl-1-(3-pyridin-4-yl-propyl)-piperidinium;
4-(2-Cyclohexyl-2-hydroxy-2-phenyl-acetoxy)-1-methyl-1-(3-pyridin-3-yl-propyl)-piperidinium;
4-(2-Cyclohexyl-2-hydroxy-2-phenyl-acetoxy)-1-(3-isoxazol-3-yl-propyl)-1-methyl-piperidinium;
4-(2-Cyclohexyl-2-hydroxy-2-phenyl-acetoxy)-1-methyl-1-phenethyl-piperidinium;
4-(2-Cyclohexyl-2-hydroxy-2-phenyl-acetoxy)-1-methyl-1-(2-pyrazin-2-yl-ethyl)-piperidinium;
4-(2-Cyclohexyl-2-hydroxy-2-phenyl-acetoxy)-1-methyl-1-(2-pyrimidin-4-yl-ethyl)-piperidinium;
4-(2-Cyclohexyl-2-hydroxy-2-phenyl-acetoxy)-1-methyl-1-(2-pyrimidin-2-yl-ethyl)-piperidinium;
4-(2-Cyclohexyl-2-hydroxy-2-phenyl-acetoxy)-1-methyl-1-(2-pyrimidin-5-yl-ethyl)-piperidinium;
4-(2-Cyclohexyl-2-hydroxy-2-phenyl-acetoxy)-1-methyl-1-(2-pyridin-2-yl-ethyl)-piperidinium;
4-(2-Cyclohexyl-2-hydroxy-2-phenyl-acetoxy)-1-methyl-1-(2-pyridin-4-yl-ethyl)-piperidinium;
4-(2-Cyclohexyl-2-hydroxy-2-phenyl-acetoxy)-1-methyl-1-(2-pyridin-3-yl-ethyl)-piperidinium;
4-(2-Cyclohexyl-2-hydroxy-2-phenyl-acetoxy)-1-(2-isoxazol-3-yl-ethyl)-1-methyl-piperidinium;
4-(2-Cyclohexyl-2-hydroxy-2-phenyl-acetoxy)-1-methyl-1-[(5-methyl-isoxazol-3-ylcarbamoyl)-methyl]-piperidinium;
4-(2-Cyclohexyl-2-hydroxy-2-phenyl-acetoxy)-1-methyl-1-(pyridazin-3-ylcarbamoylmethyl)-piperidinium;
4-(2-Cyclohexyl-2-hydroxy-2-phenyl-acetoxy)-1-methyl-1-([1,3,5]triazin-2-ylcarbamoyl-methyl)-piperidinium;
4-(2-Cyclohexyl-2-hydroxy-2-phenyl-acetoxy)-1-methyl-1-(pyrimidin-4-ylcarbamoylmethyl)-piperidinium;
4-(9-Hydroxy-9H-fluorene-9-carbonyloxy)-1-methyl-1-(3-phenyl-propyl)-piperidinium;
4-(9-Hydroxy-9H-fluorene-9-carbonyloxy)-1-methyl-1-(3-pyrazin-2-yl-propyl)-piperidinium;
4-(9-Hydroxy-9H-fluorene-9-carbonyloxy)-1-methyl-1-(3-pyrimidin-4-yl-propyl)-piperidinium;
4-(9-Hydroxy-9H-fluorene-9-carbonyloxy)-1-methyl-1-(3-pyrimidin-2-yl-propyl)-piperidinium;
4-(9-Hydroxy-9H-fluorene-9-carbonyloxy)-1-methyl-1-(3-pyrimidin-5-yl-propyl)-piperidinium;
4-(9-Hydroxy-9H-fluorene-9-carbonyloxy)-1-methyl-1-(3-pyridin-2-yl-propyl)-piperidinium;
4-(9-Hydroxy-9H-fluorene-9-carbonyloxy)-1-methyl-1-(3-pyridin-4-yl-propyl)-piperidinium;
4-(9-Hydroxy-9H-fluorene-9-carbonyloxy)-1-methyl-1-(3-pyridin-3-yl-propyl)-piperidinium;
4-(9-Hydroxy-9H-fluorene-9-carbonyloxy)-1-(3-isoxazol-3-yl-propyl)-1-methyl-piperidinium;
4-(9-Hydroxy-9H-fluorene-9-carbonyloxy)-1-methyl-1-phenethyl-piperidinium;
4-(9-Hydroxy-9H-fluorene-9-carbonyloxy)-1-methyl-1-(2-pyrazin-2-yl-ethyl)-piperidinium;
4-(9-Hydroxy-9H-fluorene-9-carbonyloxy)-1-methyl)-piperidinium;
4-(9-Hydroxy-9H-fluorene-9-carbonyloxy)-1-methyl-1-(2-pyrimidin-2-yl-ethyl)-piperidinium;
4-(9-Hydroxy-9H-fluorene-9-carbonyloxy)-1-methyl-1-(2-pyrimidin-5-yl-ethyl)-piperidinium;
4-(9-Hydroxy-9H-fluorene-9-carbonyloxy)-1-methyl-1-(2-pyridin-2-yl-ethyl)-piperidinium;
4-(9-Hydroxy-9H-fluorene-9-carbonyloxy)-1-methyl-1-(2-pyridin-4-yl-ethyl)-piperidinium;
4-(9-Hydroxy-9H-fluorene-9-carbonyloxy)-1-methyl-1-(2-pyridin-3-yl-ethyl)-piperidinium;
4-(9-Hydroxy-9H-fluorene-9-carbonyloxy)-1-(2-isoxazol-3-yl-ethyl)-1-methyl-piperidinium;
4-(9-Hydroxy-9H-fluorene-9-carbonyloxy)-1-methyl-1-[(5-methyl-isoxazol-3-ylcarbamoyl)-methyl]-piperidinium;
4-(9-Hydroxy-9H-fluorene-9-carbonyloxy)-1-methyl-1-(pyrazin-2-ylcarbamoylmethyl)-piperidinium;
4-(9-Hydroxy-9H-fluorene-9-carbonyloxy)-1-methyl-1-(pyridazin-3-ylcarbamoylmethyl)-piperidinium;
4-(9-Hydroxy-9H-fluorene-9-carbonyloxy)-1-methyl-1-([1,3,5]triazin-2-ylcarbamoylmethyl)-piperidinium;
4-(9-Hydroxy-9H-fluorene-9-carbonyloxy)-1-methyl-1-(pyrimidin-4-ylcarbamoylmethyl)-piperidinium;
4-(9-Hydroxy-9H-fluorene-9-carbonyloxy)-1-(isoxazol-3-ylcarbamoylmethyl)-1-methyl-piperidinium;
(R)-2-(2-Cyclohexyl-2-hydroxy-2-phenyl-acetoxymethyl)-1-methyl-1-(3-phenyl-propyl)-pyrrolidinium;
(R)-2-(2-Cyclohexyl-2-hydroxy-2-phenyl-acetoxymethyl)-1-methyl-1-(3-pyrazin-2-yl-propyl)-pyrrolidinium;

(R)-2-(2-Cyclohexyl-2-hydroxy-2-phenyl-acetoxymethyl)-1-methyl-1-(3-pyrimidin-4-yl-propyl)-pyrrolidinium;
(R)-2-(2-Cyclohexyl-2-hydroxy-2-phenyl-acetoxymethyl)-1-methyl-1-(3-pyrimidin-2-yl-propyl)-pyrrolidinium;
(R)-2-(2-Cyclohexyl-2-hydroxy-2-phenyl-acetoxymethyl)-1-methyl-1-(3-pyrimidin-5-yl-propyl)-pyrrolidinium;
(R)-2-(2-Cyclohexyl-2-hydroxy-2-phenyl-acetoxymethyl)-1-methyl-1-(3-pyridin-2-yl-propyl)-pyrrolidinium;
(R)-2-(2-Cyclohexyl-2-hydroxy-2-phenyl-acetoxymethyl)-1-methyl-1-(3-pyridin-4-yl-propyl)-pyrrolidinium;
(R)-2-(2-Cyclohexyl-2-hydroxy-2-phenyl-acetoxymethyl)-1-methyl-1-(3-pyridin-3-yl-propyl)-pyrrolidinium;
(R)-2-(2-Cyclohexyl-2-hydroxy-2-phenyl-acetoxymethyl)-1-(3-isoxazol-3-yl-propyl)-1-methyl-pyrrolidinium;
(R)-2-(2-Cyclohexyl-2-hydroxy-2-phenyl-acetoxymethyl)-1-methyl-1-phenethyl-pyrrolidinium;
(R)-2-(2-Cyclohexyl-2-hydroxy-2-phenyl-acetoxymethyl)-1-methyl-1-(2-pyrazin-2-yl-ethyl)-pyrrolidinium;
(R)-2-(2-Cyclohexyl-2-hydroxy-2-phenyl-acetoxymethyl)-1-methyl-1-(2-pyrimidin-4-yl-ethyl)-pyrrolidinium;
(R)-2-(2-Cyclohexyl-2-hydroxy-2-phenyl-acetoxymethyl)-1-methyl-1-(2-pyrimidin-2-yl-ethyl)-pyrrolidinium;
(R)-2-(2-Cyclohexyl-2-hydroxy-2-phenyl-acetoxymethyl)-1-methyl-1-(2-pyrimidin-5-yl-ethyl)-pyrrolidinium;
(R)-2-(2-Cyclohexyl-2-hydroxy-2-phenyl-acetoxymethyl)-1-methyl-1-(2-pyridin-2-yl-ethyl)-pyrrolidinium;
(R)-2-(2-Cyclohexyl-2-hydroxy-2-phenyl-acetoxymethyl)-1-methyl-1-(2-pyridin-4-yl-ethyl)-pyrrolidinium;
(R)-2-(2-Cyclohexyl-2-hydroxy-2-phenyl-acetoxymethyl)-1-methyl-1-(2-pyridin-3-yl-ethyl)-pyrrolidinium;
(R)-2-(2-Cyclohexyl-2-hydroxy-2-phenyl-acetoxymethyl)-1-(2-isoxazol-3-yl-ethyl)-1-methyl-pyrrolidinium;
(R)-2-(2-Cyclohexyl-2-hydroxy-2-phenyl-acetoxymethyl)-1-methyl-1-[(5-methyl-isoxazol-3-ylcarbamoyl)-methyl]-pyrrolidinium;
(R)-2-(2-Cyclohexyl-2-hydroxy-2-phenyl-acetoxymethyl)-1-methyl-1-(pyrazin-2-ylcarbamoyl-methyl)-pyrrolidinium;
(R)-2-(2-Cyclohexyl-2-hydroxy-2-phenyl-acetoxymethyl)-1-methyl-1-(pyridazin-3-ylcarbamoyl-methyl)-pyrrolidinium;
(R)-2-(2-Cyclohexyl-2-hydroxy-2-phenyl-acetoxymethyl)-1-methyl-1-([1,3,5]triazin-2-ylcarbamoylmethyl)-pyrrolidinium;
(R)-2-(2-Cyclohexyl-2-hydroxy-2-phenyl-acetoxymethyl)-1-methyl-1-(pyrimidin-4-ylcarbamoylmethyl)-pyrrolidinium;
(R)-2-(2-Cyclopentyl-2-hydroxy-2-phenyl-acetoxymethyl)-1-methyl-1-(3-phenyl-propyl)-pyrrolidinium;
(R)-2-(2-Cyclopentyl-2-hydroxy-2-phenyl-acetoxymethyl)-1-methyl-1-(3-pyrazin-2-yl-propyl)-pyrrolidinium;
(R)-2-(2-Cyclopentyl-2-hydroxy-2-phenyl-acetoxymethyl)-1-methyl-1-(3-pyrimidin-4-yl-propyl)-pyrrolidinium;
(R)-2-(2-Cyclopentyl-2-hydroxy-2-phenyl-acetoxymethyl)-1-methyl-1-(3-pyrimidin-2-yl-propyl)-pyrrolidinium;
(R)-2-(2-Cyclopentyl-2-hydroxy-2-phenyl-acetoxymethyl)-1-methyl-1-(3-pyrimidin-5-yl-propyl)-pyrrolidinium;
(R)-2-(2-Cyclopentyl-2-hydroxy-2-phenyl-acetoxymethyl)-1-methyl-1-(3-pyridin-2-yl-propyl)-pyrrolidinium;
(R)-2-(2-Cyclopentyl-2-hydroxy-2-phenyl-acetoxymethyl-1-(3-pyridin-4-yl-propyl)-pyrrolidinium;
(R)-2-(2-Cyclopentyl-2-hydroxy-2-phenyl-acetoxymethyl)-1-methyl-1-(3-pyridin-3-yl-propyl)-pyrrolidinium;
(R)-2-(2-Cyclopentyl-2-hydroxy-2-phenyl-acetoxymethyl)-1-(3-isoxazol-3-yl-propyl)-1-methyl-pyrrolidinium;
(R)-2-(2-Cyclopentyl-2-hydroxy-2-phenyl-acetoxymethyl)-1-methyl-1-phenethyl-pyrrolidinium;
(R)-2-(2-Cyclopentyl-2-hydroxy-2-phenyl-acetoxymethyl)-1-methyl-1-(2-pyrazin-2-yl-ethyl)-pyrrolidinium;
(R)-2-(2-Cyclopentyl-2-hydroxy-2-phenyl-acetoxymethyl)-1-methyl-1-(2-pyrimidin-4-yl-ethyl)-pyrrolidinium;
(R)-2-(2-Cyclopentyl-2-hydroxy-2-phenyl-acetoxymethyl)-1-methyl-1-(2-pyrimidin-2-yl-ethyl)-pyrrolidinium;
(R)-2-(2-Cyclopentyl-2-hydroxy-2-phenyl-acetoxymethyl)-1-methyl-1-(2-pyrimidin-5-yl-ethyl)-pyrrolidinium;
(R)-2-(2-Cyclopentyl-2-hydroxy-2-phenyl-acetoxymethyl)-1-methyl-1-(2-pyridin-2-yl-ethyl)-pyrrolidinium;
(R)-2-(2-Cyclopentyl-2-hydroxy-2-phenyl-acetoxymethyl)-1-methyl-1-(2-pyridin-4-yl-ethyl)-pyrrolidinium;
(R)-2-(2-Cyclopentyl-2-hydroxy-2-phenyl-acetoxymethyl)-1-methyl-1-(2-pyridin-3-yl-ethyl)-pyrrolidinium;
(R)-2-(2-Cyclopentyl-2-hydroxy-2-phenyl-acetoxymethyl)-1-(2-isoxazol-3-yl-ethyl)-1-methyl-pyrrolidinium;
(R)-2-(2-Cyclopentyl-2-hydroxy-2-phenyl-acetoxymethyl)-1-methyl-1-[(5-methyl-isoxazol-3-ylcarbamoyl)-methyl]-pyrrolidinium;
(R)-2-(2-Cyclopentyl-2-hydroxy-2-phenyl-acetoxymethyl)-1-methyl-1-(pyridazin-2-ylcarbamoyl-methyl)-pyrrolidinium;
(R)-2-(2-Cyclopentyl-2-hydroxy-2-phenyl-acetoxymethyl)-1-methyl-1-(pyridazin-3-ylcarbamoylmethyl)-pyrrolidinium;
(R)-2-(2-Cyclopentyl-2-hydroxy-2-phenyl-acetoxymethyl)-1-methyl-1-([1,3,5]triazin-2-ylcarbamoylmethyl)-pyrrolidinium;
(R)-2-(2-Cyclopentyl-2-hydroxy-2-phenyl-acetoxymethyl)-1-methyl-1-(pyrimidin-4-ylcarbamoylmethyl)-pyrrolidinium;
(R)-2-(2-Hydroxy-2,2-diphenyl-acetoxymethyl)-1-methyl-1-(3-pyrazin-2-yl-propyl)-pyrrolidinium;
(R)-2-(2-Hydroxy-2,2-diphenyl-acetoxymethyl)-1-methyl-1-(3-pyrimidin-4-yl-propyl)-pyrrolidinium;
(R)-2-(2-Hydroxy-2,2-diphenyl-acetoxymethyl)-1-methyl-1-(3-pyrimidin-2-yl-propyl)-pyrrolidinium;
(R)-2-(2-Hydroxy-2,2-diphenyl-acetoxymethyl)-1-methyl-1-(3-pyrimidin-5-yl-propyl)-pyrrolidinium;
(R)-2-(2-Hydroxy-2,2-diphenyl-acetoxymethyl)-1-methyl-1-(3-pyridin-2-yl-propyl)-pyrrolidinium;
(R)-2-(2-Hydroxy-2,2-diphenyl-acetoxymethyl)-1-methyl-1-(3-pyridin-4-yl-propyl)-pyrrolidinium;
(R)-2-(2-Hydroxy-2,2-diphenyl-acetoxymethyl)-1-methyl-1-(3-pyridin-3-yl-propyl)-pyrrolidinium;
(R)-2-(2-Hydroxy-2,2-diphenyl-acetoxymethyl)-1-(3-isoxazol-3-yl-propyl)-1-methyl-pyrrolidinium;
(R)-2-(2-Hydroxy-2,2-diphenyl-acetoxymethyl)-1-methyl-1-(2-pyrazin-2-yl-ethyl)-pyrrolidinium;
(R)-2-(2-Hydroxy-2,2-diphenyl-acetoxymethyl)-1-methyl-1-(2-pyrimidin-4-yl-ethyl)-pyrrolidinium;
(R)-2-(2-Hydroxy-2,2-diphenyl-acetoxymethyl)-1-methyl-1-(2-pyrimidin-2-yl-ethyl)-pyrrolidinium;
(R)-2-(2-Hydroxy-2,2-diphenyl-acetoxymethyl)-1-methyl-1-(2-pyrimidin-5-yl-ethyl)-pyrrolidinium;
(R)-2-(2-Hydroxy-2,2-diphenyl-acetoxymethyl)-1-methyl-1-(2-pyridin-2-yl-ethyl)-pyrrolidinium;
(R)-2-(2-Hydroxy-2,2-diphenyl-acetoxymethyl)-1-methyl-1-(2-pyridinyl-ethyl)-pyrrolidinium;
(R)-2-(2-Hydroxy-2,2-diphenyl-acetoxymethyl)-1-methyl-1-(2-pyridin-3-yl-ethyl)-pyrrolidinium;
(R)-2-(2-Hydroxy-2,2-diphenyl-acetoxymethyl)-1-(2-isoxazol-3-yl-ethyl)-1-methyl-pyrrolidinium;
(R)-2-(2-Hydroxy-2,2-diphenyl-acetoxymethyl)-1-methyl-1-[(S-methyl-isoxazol-3-ylcarbamoyl)-methyl]-pyrrolidinium;

(R)-2-(2-Hydroxy-2,2-diphenyl-acetoxymethyl)-1-methyl-1-(pyrazin-2-ylcarbamoylmethyl)-pyrrolidinium;
(R)-2-(2-Hydroxy-2,2-diphenyl-acetoxymethyl)-1-methyl-1-(pyridazin-3-ylcarbamoylmethyl)-pyrrolidinium;
(R)-2-(2-Hydroxy-2,2-diphenyl-acetoxymethyl)-1-methyl-1-([1,3,5]triazin-2-ylcarbamoyl-methyl)-pyrrolidinium;
(R)-2-(2-Hydroxy-2,2-diphenyl-acetoxymethyl)-1-methyl-1-(pyrimidin-4-ylcarbamoylmethyl)-pyrrolidinium;
(R)-2-(9-Hydroxy-9H-fluorene-9-carbonyloxymethyl)-1-methyl-1-(3-phenyl-propyl)-pyrrolidinium;
(R)-2-(9-Hydroxy-9H-fluorene-9-carbonyloxymethyl)-1-methyl-1-(3-pyrazin-2-yl-propyl)-pyrrolidinium;
(R)-2-(9-Hydroxy-9H-fluorene-9-carbonyloxymethyl)-1-methyl-1-(3-pyrimidin-4-yl-propyl)-pyrrolidinium;
(R)-2-(9-Hydroxy-9H-fluorene-9-carbonyloxymethyl)-1-methyl-1-(3-pyrimidin-2-yl-propyl)-pyrrolidinium;
(R)-2-(9-Hydroxy-9H-fluorene-9-carbonyloxymethyl)-1-methyl-1-(3-pyrimidin-5-yl-propyl)-pyrrolidinium;
(R)-2-(9-Hydroxy-9H-fluorene-9-carbonyloxymethyl)-1-methyl-1-(3-pyridin-2-yl-propyl)-pyrrolidinium;
(R)-2-(9-Hydroxy-9H-fluorene-9-carbonyloxymethyl)-1-methyl-1-(3-pyridin-4-yl-propyl)-pyrrolidinium;
(R)-2-(9-Hydroxy-9H-fluorene-9-carbonyloxymethyl)-1-methyl-1-(3-pyridin-3-yl-propyl)-pyrrolidinium;
(R)-2-(9-Hydroxy-9H-fluorene-9-carbonyloxymethyl)-1-(3-isoxazol-3-yl-propyl)-1-methyl-pyrrolidinium;
(R)-2-(9-Hydroxy-9H-fluorene-9-carbonyloxymethyl)-1-methyl-1-phenethyl-pyrrolidinium
(R)-2-(9-Hydroxy-9H-fluorene-9-carbonyloxymethyl)-1-methyl-1-(2-pyrazin-2-yl-ethyl)pyrrolidinium;
(R)-2-(9-Hydroxy-9H-fluorene-9-carbonyloxymethyl)-1-methyl-1-(2-pyrimidinyl-ethyl)-pyrrolidinium;
(R)-2-(9-Hydroxy-9H-fluorene-9-carbonyloxymethyl)-1-methyl-1-(2-pyrimidin-2-yl-ethyl)pyrrolidinium;
(R)-2-(9-Hydroxy-9H-fluorene-9-carbonyloxymethyl)-1-methyl-(2-pyrimidin-5-yl-ethyl)-pyrrolidinium;
(R)-2-(9-Hydroxy-9H-fluorene-9-carbonyloxymethyl)-1-methyl-1-(2-pyridin-2-yl-ethyl)-pyrrolidinium;
(R)-2-(9-Hydroxy-9H-fluorene-9-carbonyloxymethyl)-1-methyl-1-(2-pyridin-4-yl-ethyl)-pyrrolidinium;
(R)-2-(9-Hydroxy-9H-fluorene-9-carbonyloxymethyl)-1-methyl-1-(2-pyridin-3-yl-ethyl)-pyrrolidinium;
(R)-2-(9-Hydroxy-9H-fluorene-9-carbonyloxymethyl)-1-(2-isoxazol-3-yl-ethyl)-1-methyl-pyrrolidinium;
(R)-2-(9-Hydroxy-9H-fluorene-9-carbonyloxymethyl)-1-methyl-1-[(5-methyl-isoxazol-3-ylcarbamoyl)-methyl]-pyrrolidinium;
(R)-2-(9-Hydroxy-9H-fluorene-9-carbonyloxymethyl)-1-methyl-1-(pyrazin-2-ylcarbamoylmethyl)-pyrrolidinium;
(R)-2-(9-Hydroxy-9H-fluorene-9-carbonyloxymethyl)-1-methyl-1-(pyridazin-3-ylcarbamoyl-methyl)-pyrrolidinium;
(R)-2-(9-Hydroxy-9H-fluorene-9-carbonyloxymethyl)-1-methyl-1-([1,3,5]triazin-2-ylcarbamoylmethyl)-pyrrolidinium;
(R)-2-(9-Hydroxy-9H-fluorene-9-carbonyloxymethyl)-1-methyl-1-(pyrimidin-4-ylcarbamoylmethyl)-pyrrolidinium; and
(R)-2-(9-Hydroxy-9H-fluorene-9-carbonyloxymethyl)-1-(isoxazol-3-ylcarbamoylmethyl)-1-methyl-pyrrolidinium.

The invention also provides a process for the preparation of compounds of formula I which comprises:

(i) (A) reacting a compound of formula II

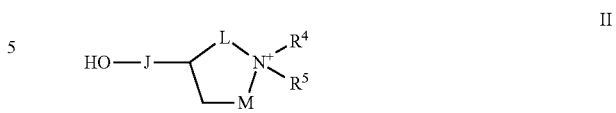

or a sodium salt thereof, where J, L, M, $R^4$ and $R^5$ are as hereinbefore defined, with a compound of formula III

or an ester-forming derivative thereof, where $R^1$, $R^2$ and $R^3$ are as hereinbefore defined; or (B) reacting a compound of formula IV

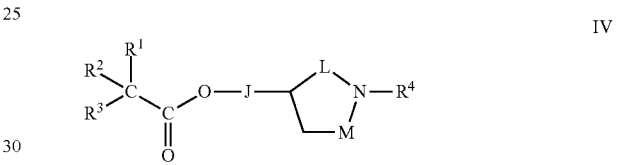

or a protected form thereof where $R^1$, $R^2$, $R^3$, $R^4$, J, L and M are as hereinbefore defined, with a compound of formula V

where $R^5$ is as hereinbefore defined and X is chloro, bromo or iodo; and (ii) recovering the product in salt or zwitterionic form.

Process variant (A) may be effected using known procedures for reacting hydroxy compounds or sodium salts thereof with carboxylic acids or ester-forming derivatives thereof such as acid halides or analogously as hereinafter described in the Examples. The reaction between an hydroxyl-substituted quinuclidine derivative and a carboxylic acid is conveniently carried out in an organic solvent, for example dimethylformamide (DMF), in the presence of a coupling agent, for example 1,1'-carbonyldiimidazole (CDI), preferably in an inert atmosphere, for example under argon. Suitable reaction temperatures are from 0° C. to 60° C., preferably from 30° C. to 50° C., especially about 40° C.

Process variant (B) may be effected using known procedures for reacting saturated heterocyclic amines with halogenides or analogously as hereinafter described in the Examples. The reaction is conveniently carried out in an organic solvent, for example dimethylsulphoxide, dimethylformamide, ether, acetonitrile or acetone. The reaction is carried out at a temperature between 20° C. to 120° C., conveniently between room temperature and 80° C.

Compounds of formula II or III are known or may be prepared by known procedures or analogously as hereinafter described in the Examples.

Compounds of formula IV may exist in individual optically active isomeric forms or as mixtures thereof, e.g. as racemic or diastereomeric mixtures. Preferred compounds of formula IV are compounds of formula IVa or IVb

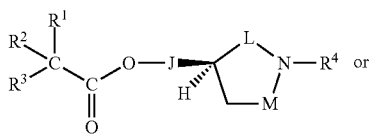

IVa

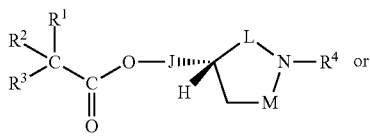

IVb or a protected form thereof where $R^1$, $R^2$, $R^3$, $R^4$, J, L and M are as hereinbefore defined.

When a compound of formula IV is a single enantiomer or is achiral, alkylation of the tertiary amine to give a compound of formula I results in a mixture of two diastereoisomers. These isomers may be separated by conventional techniques, e.g. by fractional crystallization or column chromatography.

Compounds of formula IV are known or may be prepared by reacting a compound of formula VI

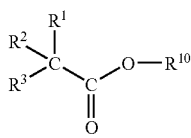

VI or a protected form thereof where $R^1$, $R^2$ and $R^3$ are as hereinbefore defined and $R^{10}$ is $C_1$-$C_4$-alkyl, with a compound of formula VII

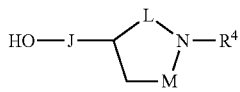

VII where $R^4$, J, L and M are as hereinbefore defined. The reaction may be effected using known procedures for reacting carboxylic esters with alcohols or analogously as hereinafter described in the Examples. The reaction is conveniently carried out in an organic solvent, for example cyclohexane or toluene, preferably in the presence of an alkali metal e.g. sodium and under an inert atmosphere such as argon. The reaction may be carried out at a temperature between 40° C. to 120° C., but preferably under reflux conditions.

Compounds of formula IV where $R^2$ is hydroxyl may be prepared by reacting a compound of formula VIII

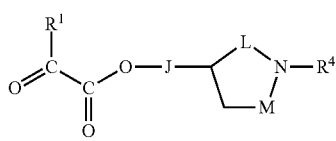

VIII or a protected form thereof where $R^1$, $R^4$, J, L and M are as hereinbefore defined, with a compound of formula IX $$XMg-R^3 \quad\quad IX$$

where $R^3$ is as hereinbefore defined and X is chloro, bromo or iodo.

Compounds of formula V or VI are known or may be prepared by known procedures or analogously as hereinafter described in the Examples.

Compounds of formula VII are known or may be prepared by alkylating the corresponding secondary amine. For example compounds of formula VII where $R^4$ is methyl may be prepared by reacting a compound of formula X

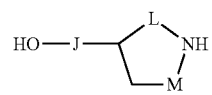

X where J, L and M are as hereinbefore defined with formaldehyde in the presence of formic acid. The reaction is conveniently carried out in a solvent, for example water, at a temperature from 40° C. to 120° C., but preferably about 80° C.

Compounds of formula VIII may be prepared by reacting a compound of formula VII where $R^4$, J, L and M are as hereinbefore defined, with a compound of formula XI

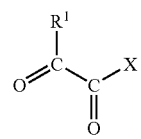

XI where $R^1$ is as hereinbefore defined and X is chloro, bromo or iodo.

Compounds of formula IX, X or XI are known or may be prepared by known procedures, or analogously as hereinafter described in the Examples.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Compounds of formula I are quaternary ammonium salts and may be converted between different salt forms using ion exchange chromatography. The compounds can be obtained in the form of hydrates' or solvates containing a solvent used for crystallization. Compounds of formula I can be recovered from reaction mixtures and purified using known methods. The compounds are initially isolated as diastereomeric mixtures however in most cases they are preferably used in pharmaceutical compositions of the invention as single enantiomers or diastereoisomers.

Compounds of formula I in pharmaceutically acceptable salt or zwitterionic form, hereinafter referred to alternatively as agents of the invention, are useful as pharmaceuticals. Accordingly the invention also provides a compound of formula I in pharmaceutically acceptable salt or zwitterionic form for use as a pharmaceutical. The agents of the invention act as muscarinic antagonists, particularly muscarinic M3 receptor antagonists thereby acting as inhibitors of bronchoconstriction.

The affinity (Ki) of agents of the invention at the human muscarinic acetylcholine M3 receptor can be determined in a competitive filtration binding assay with the radio-labelled antagonist [$^3$H]n-methyl scopolamine methyl chloride (NMS):

Membranes prepared from CHO cells stably are transfected with human M3 receptor at 10 µg protein/well then incubated with serial dilutions of the agents of the invention, [$^3$H]NMS at Kd concentration (0.25 nM) and assay buffer (20 mmol HEPES, 1 mmol MgCl$_2$ at pH 7.4) for 17 hours at room temperature. The assay is carried out in a 250 µL final volume, in the presence of a final dimethyl sulfoxide concentration of 1%. Total binding of [$^3$H]NMS is determined in the absence of the agents of the invention with a corresponding substituted volume of assay buffer. Non-specific binding of [$^3$H]NMS is determined in the presence of 300 nM ipratropium bromide. Following the incubation period, the membranes are harvested onto a Unifilter™ GF/B filter plate containing 0.05% polyethyleneimine, using a Brandel™ filtration harvester 9600. Filter plates are dried for two hours at 35° C. before the addition of Microscint™ 'O' cocktail, and are read on a Packard Topcount™ scintillator using a $^3$H-Scintillation protocol. All IC50s are calculated with the aid of XL-Fit graph package and K; values are derived using the Cheng-Prusoff correction (Cheng Y., Prusoff W. H. (1973) *Biochem. Pharmacol.* 22 3099-3109).

The compounds of the Examples hereinbelow generally have IC$_{50}$ values below 1 µM in the above assay.

Having regard to their inhibition of acetyl choline binding to M3 muscarinic receptors, agents of the invention are useful in the treatment of conditions mediated by the muscarinic M3 receptor, particularly those associated with increased parasympathetic tone leading to, for example, excessive glandular secretion or smooth muscle contraction. Treatment in accordance with the invention may be symptomatic or prophylactic.

Having regard to their antimuscarinic activity, the agents of the invention are useful in the relaxation of bronchial smooth muscle and the relief of bronchoconstriction. Relief of bronchoconstriction can be measured in models such as the in vivo plethysmography models of Chong et al, *J. Pharmacol. Toxicol. Methods* 1998, 39, 163, Hammelmann et al, *Am. J. Respir. Crit. Care Med.*, 1997, 156, 766 and analogous models. The agents of the invention are therefore useful in the treatment of obstructive or inflammatory airways diseases. In view of their long duration of action, it is possible to administer the agents of the invention once-a-day in the treatment of such diseases. In another aspect, agents of the invention commonly exhibit characteristics indicating a low incidence of side effects commonly encountered with $\beta_2$ agonists such as tachycardia, tremor and restlessness, such agents accordingly being suitable for use in on demand (rescue) treatment as well as prophylactic treatment of obstructive or inflammatory airways diseases.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, cystic fibrosis, ptilosis, siderosis, silicosis, tabacosis and byssinosis.

Having regard to their antimuscarinic activity, the agents of the invention are also useful in the treatment of a condition requiring relaxation of smooth muscle of the uterus, bladder or vascular system. They are thus useful for the prevention or alleviation of premature labour pains in pregnancy. They are also useful in the treatment of chronic and acute urticaria, psoriasis, allergic conjunctivitis, actinitis, rhinitis including allergic rhinitis, mastocytosis, urinary disorders such as urinary incontinence (particularly that caused by an overactive bladder), pollakiuria, neurogenic or unstable bladder, cytospasm and chronic cystitis; gastrointestinal disorders such as irritable bowel syndrome, spastic colitis, diverticulitis and peptic ulceration; and cardiovascular disorders such as vagally induced sinus bradycardia, as well as in ophthalmic interventions.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more the other drug substances in a fixed pharmaceutical composition or it may be administered separately, before, simultaneously with or after the other drug substance(s). Accordingly the invention includes a combination of an agent of the invention as hereinbefore described with an anti-inflammatory, bronchodilatory, antihistamine, decongestant or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM5541UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/39544, WO 03/104204, WO 03/104205, WO 04/000814, WO 04/000839, WO 04/005258 WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030725, WO 05/030212, WO 05/087744, WO 05/087745, WO 05/087749 and WO 05/090345; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408, WO 04/039762, WO 04/039766, WO 04/045618 and WO 04/046083; and $A_{2B}$ antagonists such as those described in WO 02/42298.

The agents of the invention are useful in combination therapy with chemokine receptor antagonists, calcium channel blockers, alpha-adrenoceptor antagonists, dopamine agonists, endothelin antagonists, substance-P antagonists, 5-LO inhibitors, VLA-4 antagonists and theophylline.

The agents of the invention are also particularly useful as co-therapeutic agents for use in combination with beta-2 adrenoceptor agonists. Suitable beta-2 adrenoceptor agonists include albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, especially a compound of formula

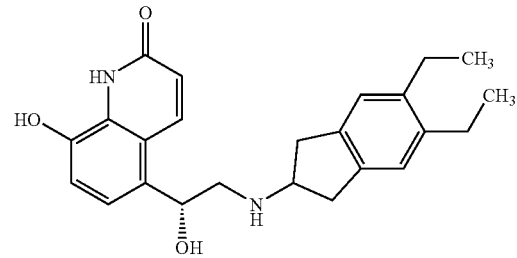

and pharmaceutically acceptable salts thereof, as well as compounds (in free or salt or solvate form) of formula I of WO 04/16601, and also compounds of EP 147719, EP 1440966, EP1460064, EP 1477167, JP 05025045, WO 93/18007, WO 99/64035, US 2002/0055651, US 2004/0242622, US 2004/0229904, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/089892, WO 04/108675, WO 04/108676, WO 05/033121, WO 05/040103, WO 05/044787, WO 05/058867, WO 05/065650, WO 05/066140 and WO 05/07908

Co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and one or more of beta-2 adrenoceptor agonists, steroids, PDE4 inhibitors, A2a agonists, A2b antagonists and LTD4 antagonists may be used, for example, in the treatment of airways diseases, including asthma and particularly COPD. Preferred triple combinations comprise an agent of the invention, a beta-2 adrenoceptor agonist and a steroid.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising a compound of formula I in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture e.g. magnesium stearate, typically 0.05-2.0% magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

All compounds of these examples are initially isolated as mixtures of diastereoisomers at the quaternary nitrogen atom. Where an individual diastereoisomer is indicated in these examples it is isolated by fractional crystallisation of such a mixture. The stereochemistry of these single isomers is determined by nmr and/or xray crystallography.

Especially preferred compounds of formula I include compounds of formula XII

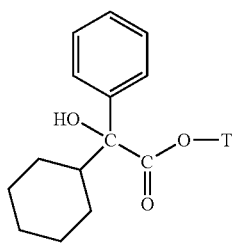

where T is as shown in Table 1 below, the method of preparation being described hereinafter. All compounds are quaternary ammonium salts. The table also shows mass spectrometry data. The relevant counter ion is identified in the relevant method of preparation.

TABLE 1

| Ex. | T | M/s M+ |
|---|---|---|
| 1 | | 456.5 |
| 2 | | 456.5 |
| 3 | | 456.2 |
| 4 | | 467.2 |

Further especially preferred compounds of formula I are compounds of formula XIII

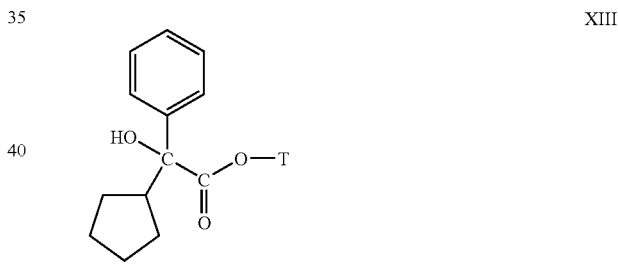

where T is as shown in Table 2 below, the methods of preparation being described hereinafter. All compounds are quaternary ammonium salts. The table also shows mass spectrometry data. The relevant counter ion is identified in the relevant method of preparation.

TABLE 2

| Ex. | T | M/s M+ |
|---|---|---|
| 5 | | 442.4 |
| 6 | | 442.5 |

TABLE 2-continued

| Ex. | T | M/s M+ |
|---|---|---|
| 7 | 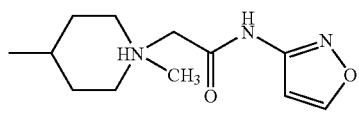 | 442.2 |
| 8 | 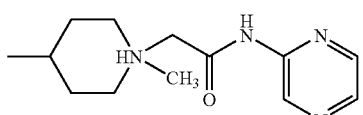 | 453.2 |
| 9 | 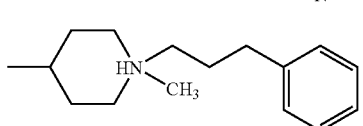 | 436.5 |
| 10 | 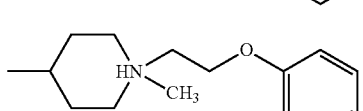 | 438.5 |

Further especially preferred compounds of formula I include compounds of formula XIV

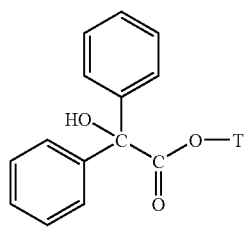

XIV where T is as shown in Table 3 below, the methods of preparation being described hereinafter. All compounds are quaternary ammonium salts. The table also shows mass spectrometry data. The relevant counterion is identified in the relevant method of preparation.

TABLE 3

| Ex. | T | M/s M+ |
|---|---|---|
| 11 | 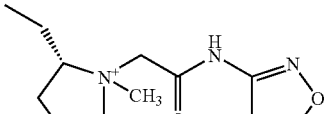 | 450.4 |
| 12 | 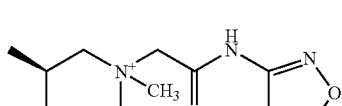 | 450.5 |
| 13 | 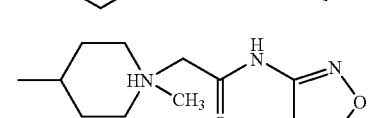 | 450.1 |

TABLE 3-continued

| Ex. | T | M/s M+ |
|---|---|---|
| 14 | 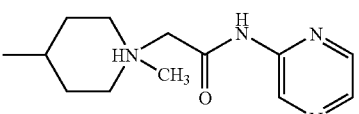 | 461.2 |
| 15 | 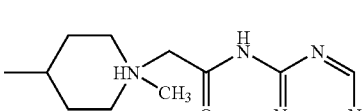 | 462.2 |

Further especially preferred compounds of formula I include compounds of formula XV

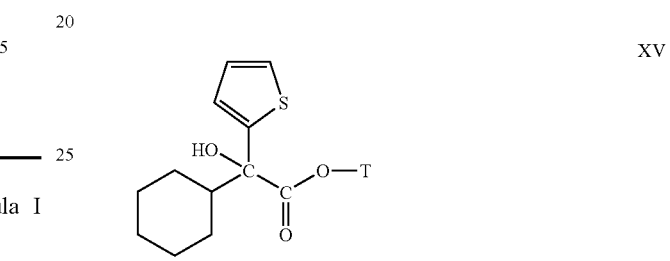

XV where T is as shown in Table 4 below, the methods of preparation being described hereinafter. Both compounds are quaternary ammonium salts. The table also shows mass spectrometry data. The relevant counterion is identified in the relevant method of preparation.

TABLE 4

| Ex. | T | M/s M+ |
|---|---|---|
| 16 | 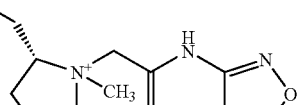 | 462.4 |
| 17 | 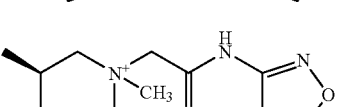 | 462.4 |

Yet further especially preferred compounds of formula I include compounds of formula XVI

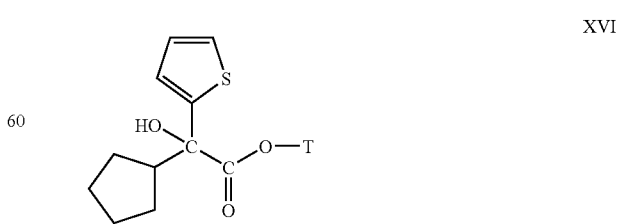

XVI where T is as shown in Table 5 below, the methods of preparation being described hereinafter. Both compounds are quaternary ammonium salts. The table also shows mass spectrometry data. The relevant counterion is identified in the relevant method of preparation.

TABLE 5

| Ex. | T | M/s M+ |
|---|---|---|
| 18 | (structure) | 448.5 |
| 19 | (structure) | 448.4 |

Yet further especially preferred compounds of formula I include compounds of formula XVII

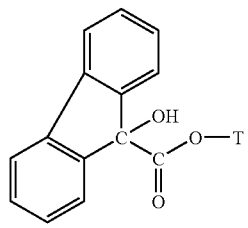

XVII where T is as shown in Table 6 below, the methods of preparation being described hereinafter. Both compounds are quaternary ammonium salts. The table also shows mass spectrometry data. The relevant counterion is identified in the relevant method of preparation.

TABLE 6

| Ex. | T | M/s M+ |
|---|---|---|
| 20 | (structure) | 448.2 |
| 21 | (structure) | 448.4 |

Preparation of Intermediate Compounds

Abbreviations used are as follows: DCM is dichloromethane, DMF is dimethylformamide, and DMSO is dimethylsulfoxide, HPLC is high performance liquid chromatography, THF is tetrahydrofuran, LC-MS is liquid chromatography mass spectrometry, CDI is 1,1'-carbonyldiimidazole.

Intermediate A

2-Bromo-N-isoxazol-3-yl-acetamide

To a stirred solution of bromoacetylbromide (5.36 ml, 61.6 mmol) in diethylether (100 ml) at −40° C. is added, dropwise over 20 minutes, a solution of 3-aminoisoxazol (5.0 ml, 67.0 mmol) and triethylamine (8.5 ml, 61.4 mmol) in diethylether (20 ml). Additional diethylether (50 ml) is added and stirring continued for 3 hours. The reaction mixture is filtered and the solution then washed with 1 M sodium carbonate solution, 1 M hydrochloric acid and brine. Concentration followed by purification by flash silica column chromatography (ethyl acetate/iso-hexane 4:7) gives the title compound as a white solid.

Intermediate B (1R/S,2R)-2-Hydroxymethyl-1-(isoxazol-3-ylcarbamoylmethyl)-1-methyl-pyrrolidinium bromide Step B1: (R)-Pyrrolidine-1,2-dicarboxylic acid 2-tert-butyl ester 1-ethyl ester (R)-Pyrrolidine-2-carboxylic acid tert-butyl ester (16.11 g, 94.1 mmol) in DCM (250 ml) under an inert atmosphere of argon is treated with triethyl amine (26 ml, 188 mmol) and then cooled to 0° C. with a ice bath. To this cooled solution is added dropwise ethyl chloroformate (8.99 ml, 94.1 mmol) and the reaction mixture is left to stir at 0° C. for 3 hours. The reaction mixture is washed with 1M HCl (2×100 ml), water, brine, dried over MgSO$_4$ and concentrated in vacuo to yield the titled compound as a clear oil.

Step B2: ((R)-1-Methyl-pyrrolidin-2-yl)-methanol

A cooled (0° C.); stirred solution of lithium aluminium hydride (200 ml of a 1 M solution in THF, 207 mmol) is treated via canula, dropwise with (R)-pyrrolidine-1,2-dicarboxylic acid 2-tert-butyl ester 1-ethyl ester (22.86 g, 94.1 mmol) in THF (300 ml). After addition, the reaction mixture is left to warm to room temperature whilst stirring over night. The solution is then treated with Rochelles salt (10 g) to partially quench the reaction and after 30 minutes, the reaction mixture is cooled (0° C.) and water (50 ml) is added dropwise, ensuring that the temperature does not exceed 10° C. The solvent is removed in vacuo and the residue is taken up in chloroform: isopropyl alcohol (300 ml of a 7:3 mixture) and left to stir at room temperature for 3 hours. The resulting suspension is removed by filtration and the filtrate is concentrated in vacuo. The resulting oil is purified by distillation on Kugelrohr to yield the titled compound as a clear oil.

Step B3: (1R/S,2R)-2-Hydroxymethyl-1-(isoxazol-3-ylcarbamoylmethyl)-1-methyl-pyrrolidinium bromide To a solution of 2-bromo-N-isoxazol-3-yl-acetamide (Intermediate A) (3.9 g, 191 mmol) in acetonitrile (95 ml) is added ((R)-1-methyl-pyrrolidin-2-yl)-methanol (2.2 g, 191 mmol) in acetonitrile (5 ml). The reaction mixture is stirred at room temperature for 3 hours and then the solvent is removed in vacuo. The resulting oil is taken up in acetonitrile and ethyl acetate is then added. The resulting cloudy solution is stirred at room temperature for 30 minutes. There after, the supernatant is decanted off and the solid is dried under vacuum over two days to afford the titled compound.

Intermediate C (1R/S,2R)-3-Hydroxy-1-(isoxazol-3-ylcarbamoylmethyl)-1-methyl-piperidinium bromide

Step C1: (R)-3-Hydroxy-piperidine-1-carboxylic acid tert-butyl ester

To a cooled (0° C.) solution comprising (R)-3-hydroxy piperidine hydrochloride (5.0 g, 36.3 mmol) in water/dioxane (200 ml of a 1:1 mixture) is added sodium hydrogen carbonate (10.7 g, 127 mmol) followed by di-t-butyl dicarbonate (9.11 g, 41.7 mmol), portionwise. The reaction mixture is allowed to warm to room temperature and stirred for 2 days. The resulting suspension is filtered through Celite® filter material and washed with dioxane. The filtrate is concentrated in vacuo to remove half the solvent and then acidified to pH 3 with 2M citric acid. This solution is extracted with DCM (3×100 ml) and the combined organic extracts are dried (MgSO$_4$) and concentrated in vacuo to yield the titled product as a brown oil.

Step C2: (R)-1-Methyl-piperidin-3-ol

This compound is prepared by an analogous method to ((R)-1-Methyl-pyrrolidin-2-yl)-methanol (Step B2) by replacing (R)-pyrrolidine-1,2-dicarboxylic acid 2-tert-butyl ester 1-ethyl ester (Step B1) with (R)-3-Hydroxy-piperidine-1-carboxylic acid tert-butyl ester (Step C1).

Step C3: (1R/S,3R)-3-Hydroxy-1-(isoxazol-3-ylcarbamoylmethyl)-1-methyl-piperidinium bromide (R)-1-Methyl-piperidin-3-ol (1.15 g, 10 mmol) and 2-bromo-N-isoxazol-3-yl-acetamide (Intermediate A) (2.25 g, 11 mmol) are stirred together in chloroform/acetonitrile (20 ml of a 1:1 mixture) at room temperature for 1 hour. The solvent is removed in vacuo and the resulting oil is purified using C-18 reverse phase column chromatography (eluent-water:acetonitrile from 0% to 30% acetonitrile) to yield the titled compound.

Intermediate D

Cyclopentyl-H-hydroxy-thiophen-2-yl-acetic acid

To a stirred suspension of magnesium (0.232 g, 9.7 mmol) in ether (5 ml) under an atmosphere of argon is added iodine (catalytic amount). After 5 minutes, the reaction mixture is treated with cyclopentyl bromide (2 ml, 9.7 mmol) in ether (5 ml) portionwise over 10 minutes and is then stirred at room temperature for 20 minutes. Meanwhile, a second reaction vessel comprising 2-thiopheneglyoxcylic acid (1 g, 6.5 mmol) in ether (10 ml) cooled to 0° C. is treated with sodium hydride (0.26 g of a 60% dispersion in mineral oil, 6.5 mmol). The reaction mixture is stirred for 30 minutes and then the grignard reagent (prepared as described above) is added portion wise over 5 minutes. After stirring at room temperature for 4 hours, the reaction mixture is partitioned between water (100 ml) and ethyl acetate (100 ml). The aqueous layer is acidified to pH 1 with 1M hydrochloric acid and then extracted with ethyl acetate (50 ml). The organic portions are combined, washed with brine, dried over magnesium sulphate and evaporated in vacuo, to yield the titled compound as a yellow solid.

Intermediate E

Cyclohexyl-hydroxy-thiophen-2-yl-acetic acid

This compound is prepared by a method that is analogous to that used to prepare cyclopentyl-H-hydroxy-thiophen-2-yl-acetic acid (Intermediate D) by replacing cyclopentyl magnesium bromide with cyclohexyl magnesium bromide.

Intermediate F

Hydroxy-diphenyl-acetic acid 1-methyl-piperidin-4-yl ester

A mixture comprising 1-methyl-piperidin-4-ol (20 g, 170 mmol) and methyl benzylate (63.1 g, 250 mmol) in cyclohexane (300 ml) is heated to 60° C. and treated with sodium (0.39 g, 17 mmol) in small portions. The reaction mixture is then heated to 85° C. for 5 hours and then allowed to cool to room temperature overnight. The mixture is filtered and the solid is washed with cyclohexane. The resulting crude residue is dried under vacuum and recrystallised from hot acetonitrile to yield the titled compound.

Intermediate G

2-Bromo-N-pyrazin-2-yl-acetamide

This compound is prepared by an analogous method to 2-bromo-N-isoxazol-3-yl-acetamide (Intermediate A) by replacing 3-aminoisoxazole with 2-aminopyrazine

Intermediate H

4-Hydroxy-1-methyl-1-(pyrazin-2-ylcarbamoylmethyl)-piperidinium bromide

This compound is prepared by an analogous method to (1R/S,3R)-3-Hydroxy-1-(isoxazol-3-ylcarbamoylmethyl)-1-methyl-piperidinium bromide (Intermediate C) by replacing (R)-1-methyl-piperidin-3-ol (step C3) with 1-methyl-piperidin-4-ol and by replacing 2-bromo-N-isoxazol-3-yl-acetamide (Intermediate A) with 2-bromo-N-pyrazin-2-yl-acetamide (Intermediate G).

Intermediate I

4-Hydroxy-1-(isoxazol-3-ylcarbamoylmethyl)-1-methyl-piperidinium bromide

This compound is prepared by an analogous method to (1R/S,3R)-3-Hydroxy-1-(isoxazol-3-ylcarbamoylmethyl)-1-methyl-piperidinium bromide (Intermediate C) by replacing (R)-1-methyl-piperidin-3-ol (step C3) with 1-methyl-piperidin-4-ol.

Intermediate J

2-Bromo-N-[1,3,5]triazin-2-yl-acetamide

This compound is prepared by an analogous method to 2-bromo-N-isoxazol-3-yl-acetamide (Intermediate A) by replacing 3-aminoisoxazole with [1,3,5]triazin-2-ylamine.

Intermediate K

4-Hydroxy-1-methyl-1-(3-phenyl-propyl)-piperidinium bromide

This compound is prepared by an analogous method to (1R/S,3R)-3-Hydroxy-1-(isoxazol-3-ylcarbamoylmethyl)-1-methyl-piperidinium bromide (Intermediate C) by replacing (R)-1-methyl-piperidin-3-ol (step C3) with 1-methyl-piperidin-4-ol and by replacing 2-bromo-N-isoxazol-3-yl-acetamide (Intermediate A) with 3-phenyl propylbromide.

Intermediate L

4-Hydroxy-1-methyl-1-(2-phenoxy-ethyl)-piperidinium bromide

This compound is prepared by an analogous method to (1R/S,3R)-3-Hydroxy-1-(isoxazol-3-ylcarbamoylmethyl)-1-methyl-piperidinium bromide (Intermediate C) by replacing (R)-1-methyl-piperidin-3-ol (step C3) with 1-methyl-piperidin-4-ol and by replacing 2-bromo-N-isoxazol-3-yl-acetamide (Intermediate A) with 2-phenoxy-ethylbromide.

Preparation of Specific Examples

Example 1

(1R/S,2R)-2-((R/S)-(2-Cyclohexyl-2-hydroxy-2-phenyl-acetoxymethyl)-1-(isoxazol-3-yl carbamoyl-methyl)-1-methyl-pyrrolidinium bromide

To a solution comprising (1R/S,2R)-2-hydroxymethyl-1-(isoxazol-3-ylcarbamoylmethyl)-1-methyl-pyrrolidinium bromide (Intermediate B) (0.230 g, 0.718 mmol) in DMF (2 ml) is added sodium hydride (0.057 g, of a 60% dispersion in oil, 1.44 mmol) in one portion. The suspension is stirred at room temperature for 2 hours. Meanwhile, in a second reaction vessel, a solution of cyclohexyl-hydroxy-phenyl-acetic acid (0.160 g, 0.68 mmol) in DMF (2 ml) is treated with CDI (0.11 g, 0.68 mmol) in one portion. The reaction mixture is stirred at room temperature for 2 hours. The resulting CDI intermediate is added to the reaction vessel containing the sodium salt of (1R/S,2R)-2-hydroxymethyl-1-(isoxazol-3-ylcarbamoylmethyl)-1-methyl-pyrrolidinium bromide and the reaction mixture is stirred at room temperature for 2.5 hours. The reaction mixture is diluted with water (2 ml) and 0.13 ml of HBr (48% solution in water) and purified using C-18 reverse phase column chromatography (eluent-water: acetonitrile from 0% to 100% acetonitrile) to yield the titled compound.

Example 2

(1R/S,3R)-3-((R/S)-(2-Cyclohexyl-2-hydroxy-2-phenyl-acetoxy)-1-(isoxazol-3-ylcarbamoyl-methyl)-1-methyl-piperidinium bromide

This compound is prepared by an analogous method to (1R/S,2R)-2-((R/S)-(2-Cyclohexyl-2-hydroxy-2-phenyl-acetoxymethyl)-1-(isoxazol-3-yl carbamoylmethyl)-1-methyl-pyrrolidinium bromide (Example 1) by replacing (1R/S,2R)-2-hydroxymethyl-1-(isoxazol-3-ylcarbamoyl-methyl)-1-methyl-pyrrolidinium bromide (Intermediate B) with (1R/S,2R)-3-Hydroxy-1-(isoxazol-3-ylcarbamoylmethyl)-1-methyl-piperidinium bromide (Intermediate C).

Example 3

4-(2-Cyclohexyl-2-hydroxy-2-phenyl-acetoxy)-1-(isoxazol-3-ylcarbamoylmethyl)-1-methyl-piperidinium bromide

This compound is prepared by an analogous method to (1R/S,2R)-2-((R/S)-(2-Cyclohexyl-2-hydroxy-2-phenyl-acetoxymethyl)-1-(isoxazol-3-yl carbamoylmethyl)-1-methyl-pyrrolidinium bromide (Example 1) by replacing (1R/S,2R)-2-hydroxymethyl-1-(isoxazol-3-ylcarbamoyl-methyl)-1-methyl-pyrrolidinium bromide (Intermediate B) with 4-hydroxy-1-(isoxazol-3-ylcarbamoylmethyl)-1-methyl-piperidinium bromide (Intermediate I).

Example 4

4-(2-Cyclohexyl-2-hydroxy-2-phenyl-acetoxy)-1-methyl-1-(pyrazin-2-ylcarbamoylmethyl)-piperidinium bromide

This compound is prepared by an analogous method to (1R/S,2R)-2-((R/S)-(2-Cyclohexyl-2-hydroxy-2-phenyl-acetoxymethyl)-1-(isoxazol-3-yl carbamoylmethyl)-1-methyl-pyrrolidinium bromide (Example 1) by replacing (1R/S,2R)-2-hydroxymethyl-1-(isoxazol-3-ylcarbamoyl-methyl)-1-methyl-pyrrolidinium bromide (Intermediate B) with 4-hydroxy-1-methyl-1-(pyrazin-2-ylcarbamoylmethyl)-piperidinium bromide (Intermediate H).

Example 5

(1R/S,2R)-2-((R/S)-(2-Cyclopentyl-2-hydroxy-2-phenyl-acetoxymethyl)-1-(isoxazol-3-ylcarbamoyl-methyl)-1-methyl-pyrrolidinium bromide

This compound is prepared by an analogous method to (1R/S,2R)-2-((R/S)-(2-Cyclohexyl-2-hydroxy-2-phenyl-acetoxymethyl)-1-(isoxazol-3-ylcarbamoylmethyl)-1-methyl-pyrrolidinium bromide (Example 1) by replacing cyclohexyl-hydroxy-phenyl-acetic acid with cyclopentyl-mandelic acid.

Example 6

(1R/S,3R)-3-((R/S)-(2-Cyclopentyl-2-hydroxy-2-phenyl-acetoxy)-1-(isoxazol-3-ylcarbamoyl-methyl)-1-methyl-piperidinium bromide

This compound is prepared by an analogous method to (1R/S,2R)-3-((R/S)-(2-cyclohexyl-2-hydroxy-2-phenyl-acetoxy)-1-(isoxazol-3-ylcarbamoylmethyl)-1-methyl-piperidinium bromide (Example 2) by replacing cyclohexyl-hydroxy-phenyl-acetic acid with cyclopentyl-mandelic acid.

Example 7

4-(2-Cyclopentyl-2-hydroxy-2-phenyl-acetoxy)-1-(isoxazol-3-ylcarbamoyl methyl)-1-methyl-piperidinium bromide

This compound is prepared by an analogous method to 4-(2-cyclohexyl-2-hydroxy-2-phenyl-acetoxy)-1-(isoxazol-3-ylcarbamoylmethyl)-1-methyl-piperidinium bromide (Example 3) by replacing cyclohexyl-hydroxy-phenyl-acetic acid with cyclopentyl-mandelic acid.

Example 8

4-(2-Cyclopentyl-2-hydroxy-2-phenyl-acetoxy-1-methyl-1-(pyrazin-2-ylcarbamoylmethyl)-piperidinium bromide This compound is prepared by an analogous method to 4-(2-cyclohexyl-2-hydroxy-2-phenyl-acetoxy)-1-methyl-1-(pyrazin-2-ylcarbamoylmethyl)-piperidinium bromide (Example 4) by replacing cyclohexyl-hydroxy-phenyl-acetic acid with cyclopentyl-mandelic acid.

Example 9

4-((R)-2-Cyclopentyl-2-hydroxy-2-phenyl-acetoxy)-1-methyl-1-(3-phenyl-propyl)-piperidinium bromide This compound is prepared by an analogous method to (1R/S,2R)-2-((R/S)-(2-Cyclohexyl-2-hydroxy-2-phenyl-acetoxymethyl)-1-(isoxazol-3-ylcarbamoylmethyl)-1-methyl-pyrrolidinium bromide (Example 1) by replacing (1R/S,2R)-2-hydroxymethyl-1-(isoxazol-3-ylcarbamoyl-methyl)-1-methyl-pyrrolidinium bromide (Intermediate B) with 4-Hydroxy-1-methyl-1-(3-phenyl-propyl)-piperidinium bromide (Intermediate K) and by replacing cyclohexyl-hydroxy-phenyl-acetic acid with cyclopentyl-mandelic acid.

Example 10

4-((R)-2-Cyclopentyl-2-hydroxy-2-phenyl-acetoxy)-1-methyl-1-(2-phenoxy-ethyl)-piperidinium bromide This compound is prepared by an analogous method to 4-((R)-2-Cyclopentyl-2-hydroxy-2-phenyl-acetoxy)-1-methyl-1-(3-phenyl-propyl)-piperidinium bromide (Example 9) by replacing 4-Hydroxy-1-methyl-1-(3-phenyl-propyl)-piperidinium bromide (Intermediate K) with 4-hydroxy-1-methyl-1-(2-phenoxy-ethyl)-piperidinium bromide (Intermediate L).

Example 11

(1R/S,2R)-2-(2-Hydroxy-2,2-diphenyl-acetoxymethyl)-1-(isoxazol-3-ylcarbamoyl methyl)-1-methyl-pyrrolidinium bromide This compound is prepared by an analogous method to (1R/S,2R)-2-((R/S)-(2-Cyclohexyl-2-hydroxy-2-phenyl-acetoxymethyl)-1-(isoxazol-3-ylcarbamoylmethyl)-1-methyl-pyrrolidinium bromide (Example 1) by replacing cyclohexyl-hydroxy-phenyl-acetic acid with benzilic acid

Example 12

(1R/S,3R)-3-(2-Hydroxy-2,2-diphenyl-acetoxymethyl)-1-(isoxazol-3-ylcarbamoyl methyl)-1-methyl-piperidinium bromide This compound is prepared by an analogous method (1R/S,2R)-3-((R/S)-(2-cyclohexyl-2-hydroxy-2-phenyl-acetoxy)-1-(isoxazol-3-ylcarbamoylmethyl)-1-methyl-piperidinium bromide: (Example 2) by replacing cyclohexyl-hydroxy-phenyl-acetic acid with benzilic acid.

Example 13

4-(2-Hydroxy-2,2-diphenyl-acetoxy)-1-(isoxazol-3-ylcarbamoylmethyl)-1-methyl-piperidinium bromide To a stirred solution comprising hydroxy-diphenyl-acetic acid 1-methyl-piperidin-4-yl ester (Intermediate F) (0.25 g, 0.77 mmol) in acetonitrile (5 ml) under an inert atmosphere of argon is added 2-bromo-N-isoxazol-3-yl-acetamide (Intermediate A). The reaction mixture is stirred overnight at room temperature and then water is added. Acetonitrile is removed in vacuo and the resulting mixture is decanted into a clean flask and left overnight. The solid that formed is filtered to yield the titled product.

Example 14

4-(2-Hydroxy-2,2-diphenyl-acetoxy)-1-methyl-1-(pyrazin-2-ylcarbamoylmethyl)-piperidinium bromide This compound is prepared by an analogous method to 4-(2-Hydroxy-2,2-diphenyl-acetoxy)-1-(isoxazol-3-ylcarbamoylmethyl)-1-methyl-piperidinium bromide (Example 13) by replacing 2-bromo-N-isoxazol-3-yl-acetamide (Intermediate A) with 2-bromo-N-pyrazin-2-yl-acetamide (Intermediate G).

Example 15

4-(2-Hydroxy-2,2-diphenyl-acetoxy)-1-methyl-1-([1,3,5]-triazin-2-ylcarbamoylmethyl)-piperidinium bromide A solution comprising hydroxy-diphenyl-acetic acid 1-methyl-piperidin-4-yl ester (Intermediate F) (0.3 g, 0.9 mmol) and 2-bromo-N-[1,3,5]triazin-2-yl-acetamide (Intermediate J) (0.2 g, 0.9 mmol) in acetonitrile/chloroform (2 ml of a 1:1 mixture) is stirred under an inert atmosphere of argon at room temperature for 2 days. The titled product is observed by LC-MS. (M+462.2)

Example 16

(1R/S,2R)-2-((R/S)-(2-Cyclohexyl-2-hydroxy-2-thiophen-2-yl-acetoxymethyl)-1-(isoxazol-3-ylcarbamoylmethyl)-1-methyl-pyrrolidinium bromide This compound is prepared by an analogous method to (1R/S,2R)-2-((R/S)-(2-Cyclohexyl-2-hydroxy-2-phenyl-acetoxymethyl)-1-(isoxazol-3-ylcarbamoylmethyl)-1-methyl-pyrrolidinium bromide (Example 1) by replacing cyclohexyl-hydroxy-phenyl-acetic acid with cyclohexyl-hydroxy-thiophen-2-yl-acetic acid (Intermediate E).

Example 17

(1R/S,3R)-3-((R/S)-(2-Cyclohexyl-2-hydroxy-2-thiophen-1-acetoxymethyl)-1-(isoxazol-3-ylcarbamoylmethyl)-1-methyl-piperidinium bromide This compound is prepared by an analogous method (1R/S,2R)-3-((R/S)-(2-cyclohexyl-2-hydroxy-2-phenyl-acetoxy)-1-(isoxazol-3-ylcarbamoylmethyl)-1-methyl-piperidinium bromide: (Example 2) by replacing cyclohexylhydroxy-phenyl-acetic acid with cyclohexyl-hydroxy-thiophen-2-yl-acetic acid (Intermediate E).

Example 18

1R/S,2R)-2-((R/S)-(2-Cyclopentyl-2-hydroxy-2-thiophen-2-yl-acetoxymethyl)-1-(isoxazol-3-ylcarbamoylmethyl)-1-methyl-pyrrolidinium bromide This compound is prepared by an analogous method to (1R/S,2R)-2-((R/S)-(2-Cyclohexyl-2-hydroxy-2-phenyl-acetoxymethyl)-1-(isoxazol-3-ylcarbamoylmethyl)-1-methyl-pyrrolidinium bromide (Example 1) by replacing cyclohexyl-hydroxy-phenyl-acetic acid with cyclopentyl-H-hydroxy-thiophen-2-yl-acetic acid (Intermediate E).

Example 19

(1R/S,3R)-3-((R/S)-(2-Cyclopentyl-2-hydroxy-1-thiophen-2-yl-acetoxymethyl)-1-(isoxazol-3-ylcarbamoylmethyl)-1-methyl-piperidinium bromide This compound is prepared by an analogous method (1R/S,2R)-3-((R/S)-(2-cyclohexyl-2-hydroxy-2-phenyl-acetoxy)-1-(isoxazol-3-ylcarbamoylmethyl)-1-methyl-piperidinium bromide: (Example 2) by replacing cyclohexyl-hydroxy-phenyl-acetic acid with cyclopentyl-H-hydroxy-thiophen-2-yl-acetic acid (Intermediate E).

Example 20

(1R/S, 2R)-2-(9-Hydroxy-9H-fluorene-9-carbonyloxymethyl)-1-(isoxazol-3-ylcarbamoylmethyl)-1-methyl-pyrrolidinium This compound is prepared by an analogous method to (1R/S,2R)-2-((R/S)-(2-Cyclohexyl-2-hydroxy-2-phenyl-acetoxymethyl)-1-(isoxazol-3-ylcarbamoylmethyl)-1-methyl-pyrrolidinium bromide (Example 1) by replacing cyclohexyl-hydroxy-phenyl-acetic acid with 9-hydroxy-9-fluorene carboxylic acid.

Example 21

(1R/S, 3R)-3-(9-Hydroxy-9H-fluorene-9-carbonyloxymethyl)-1-(isoxazol-3-ylcarbamoylmethyl)-1-methyl-piperidinium This compound is prepared by an analogous method (1R/S,2R)-3-((R/S)-(2-cyclohexyl-2-hydroxy-2-phenyl-acetoxy)-1-(isoxazol-3-ylcarbamoylmethyl)-1-methyl-piperidinium bromide: (Example 2) by replacing cyclohexyl-hydroxy-phenyl-acetic acid with 9-hydroxy-9-fluorene carboxylic acid.

The invention claimed is:
1. A compound formula I

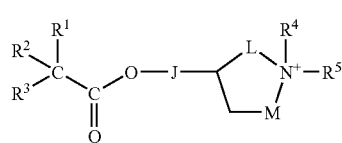

I in salt or zwitterionic form wherein
L and M are a bond and —$CH_2$—$CH_2$— and J is $C_1$-$C_2$-alkylene;
—$CR^1R^2R^3$ together form a group of formula

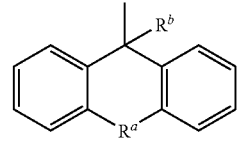

where $R^a$ is a bond, and $R^b$ is hydroxy;
$R^4$ is methyl;
$R^5$ is $C_1$-alkyl substituted by —CO—NH—$R^6$; and
$R^6$ is a $C_3$-$C_{15}$-carbocyclic group or a 5- to 12-membered heterocyclic group having at least one ring heteroatom selected from nitrogen, oxygen and sulphur.

2. A compound according to claim 1, wherein
L and M are (a bond and —$CH_2$—$CH_2$—) and J is $C_1$-$C_2$-alkylene;
—$CR^1R^2R^3$ together form a group of formula

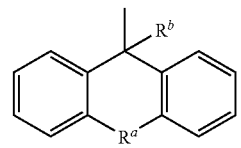

where $R^a$ is a bond, and $R^b$ is hydroxy;
$R^4$ is methyl;
$R^5$ is $C_1$-alkyl substituted by —CO—NH—$R^6$; and
$R^6$ is a $C_3$-$C_{10}$-carbocyclic group or a 5- to 9-membered heterocyclic group having at least one ring heteroatom selected from nitrogen, oxygen and sulfur.

3. A compound according to claim 1, wherein said compound is a single enantiomer.

4. A pharmaceutical composition comprising as active ingredient a compound according to claim 1.

5. A process for the preparation of a compound of formula I as claimed in claim 1 which comprises:
(i) (A) reacting a compound of formula II

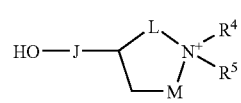

II or a sodium salt thereof, where J, L, M, $R^4$ and $R^5$ are as defined in claim 1, with a compound of formula III

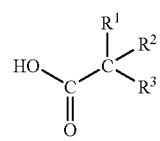

III or an ester-forming derivative thereof, where $R^1$, $R^2$, and $R^3$ are as defined in claim 2;

(B) reacting a compound of formula IV

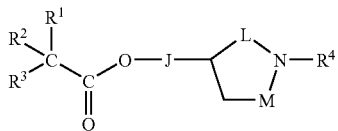

or a protected form thereof where $R^1, R^2, R^3, R^4, J, L$ and M are as defined in claim 2, with a compound of formula V

X—R⁵    V where $R^5$ is as defined in claim 2 and X is chloro, bromo iodo; and
(ii) recovering the product in salt or zwitterionic form.

6. A method of treating an inflammatory or obstructive airways disease in a subject in need of such treatment, which comprises administering to said subject an effective amount of a compound according to claim 1.

7. A method according to claim 6, wherein said inflammatory or obstructive airways disease is asthma, adult/acute respiratory distress syndrome (ARDS), chronic obstructive pulmonary or airways disease (COPD or COAD), chronic bronchitis or dyspnea associated therewith, emphysema, exacerbation of airways hyperreactivity consequent to other drug therapy, bronchitis, acute, arachidic, catarrhal, croupus, chronic or phthinoid bronchitis, pneumoconiosis, aluminosis, anthracosis, asbestosis, chalicosis, cystic fibrosis, ptilosis, siderosis, silicosis, tabacosis or byssinosis.

8. A method according to claim 7, wherein said inflammatory or obstructive airways disease is asthma or COPD.

* * * * *